(12) United States Patent
Kawano et al.

(10) Patent No.: US 8,729,191 B2
(45) Date of Patent: *May 20, 2014

(54) PRODUCTION PROCESS OF POLYACRYLIC ACID (SALT) WATER-ABSORBENT RESIN

(75) Inventors: Takaaki Kawano, Kyotanabe (JP); Hirotama Fujimaru, Himeji (JP); Kunihiko Ishizaki, Suita (JP); Katsuyuki Wada, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 619 days.

This patent is subject to a terminal disclaimer.

(21) Appl. No.: 11/883,621

(22) PCT Filed: Apr. 6, 2006

(86) PCT No.: PCT/JP2006/307792
§ 371 (c)(1),
(2), (4) Date: Aug. 2, 2007

(87) PCT Pub. No.: WO2006/109842
PCT Pub. Date: Oct. 19, 2006

(65) Prior Publication Data
US 2008/0161512 A1 Jul. 3, 2008

(30) Foreign Application Priority Data

Apr. 7, 2005 (JP) .................. 2005-110960
Apr. 7, 2005 (JP) .................. 2005-111204

(51) Int. Cl.
*C08F 6/02* (2006.01)
*C08F 8/44* (2006.01)
*C08F 20/06* (2006.01)

(52) U.S. Cl.
USPC ........ 525/330.2; 525/362; 525/371; 525/372; 526/93; 526/103; 526/208; 526/210; 526/213; 526/317.1

(58) Field of Classification Search
USPC ......... 525/330.2, 362, 371, 372; 526/93, 103, 526/208, 210, 213, 317.1
See application file for complete search history.

(56) References Cited

U.S. PATENT DOCUMENTS

| | | |
|---|---|---|
| 4,389,513 A | 6/1983 | Miyazaki |
| 4,497,930 A | 2/1985 | Yamasaki et al. ............. 524/556 |
| 4,654,039 A | 3/1987 | Brandt et al. |
| 4,985,514 A | 1/1991 | Kimura et al. |
| 5,180,798 A | 1/1993 | Nakamura et al. ............. 526/66 |
| 5,409,771 A | 4/1995 | Dahment et al. |
| 5,439,993 A | 8/1995 | Ito et al. |
| 5,562,646 A | 10/1996 | Goldman et al. |
| 5,624,967 A | 4/1997 | Hitomi et al. |
| 6,310,156 B1 | 10/2001 | Maeda et al. |
| 6,444,744 B1 | 9/2002 | Fujimaru et al. |
| 6,787,001 B2* | 9/2004 | Sakamoto et al. ............. 203/2 |
| 2002/0120085 A1 | 8/2002 | Matsumoto et al. |
| 2003/0065215 A1 | 4/2003 | Sakamoto et al. ............. 562/532 |
| 2003/0100830 A1 | 5/2003 | Zhong et al. ................... 600/431 |
| 2004/0050679 A1 | 3/2004 | Hammon et al. ................ 203/6 |
| 2004/0110897 A1 | 6/2004 | Sakamoto et al. |
| 2004/0110913 A1 | 6/2004 | Kanto et al. |
| 2004/0110914 A1 | 6/2004 | Nakahara et al. |
| 2004/0236049 A1 | 11/2004 | Fuchs et al. |
| 2005/0209411 A1 | 9/2005 | Nestler et al. |
| 2005/0222459 A1 | 10/2005 | Nordhoff et al. |
| 2006/0036043 A1 | 2/2006 | Nestler et al. |
| 2006/0074160 A1* | 4/2006 | Handa et al. ................... 524/284 |
| 2006/0089512 A1 | 4/2006 | Bennett et al. |
| 2008/0119626 A1* | 5/2008 | Fujimaru et al. ............ 526/317.1 |
| 2008/0161512 A1 | 7/2008 | Kawano et al. |

FOREIGN PATENT DOCUMENTS

| | | | |
|---|---|---|---|
| EP | 0 205 674 | 12/1986 | |
| EP | 0 942 014 | 9/1999 | |
| EP | 1 302 485 A1 | 4/2003 | |
| EP | 1 457 541 A1 | 9/2004 | |
| EP | 1577349 A1 | 9/2005 | |
| GB | 2088392 | 6/1982 | ................ C08F 2/32 |
| JP | 57-073007 | 5/1982 | |
| JP | 59-062665 | 4/1984 | |
| JP | 60-245608 | 12/1985 | |
| JP | 03-031306 | 2/1991 | |
| JP | 06-211934 | 8/1994 | |
| JP | 08-188602 | 7/1996 | |
| JP | 11-071425 | 3/1999 | |
| JP | 2000-053729 | 2/2000 | |

(Continued)

OTHER PUBLICATIONS

Pharmco Products Inc., Sodium Hydroxide 50% Product Specification Sheet (2002).*

(Continued)

*Primary Examiner* — Roberto Rabago
(74) *Attorney, Agent, or Firm* — Harness, Dickey & Pierce, P.L.C.

(57) ABSTRACT

An embodiment of the present invention allows for production, with a high productivity, of a water-absorbent resin including an improved relationship between absorption capacity and water-soluble polymer which are conflicting properties of the water-absorbent resin, being easily controlled for polymerization reaction, being of no odor, being less colored, and being of high absorption properties. In one embodiment of the present invention, acrylic acid composition is neutralized with a basic composition including an iron content of 0.2 to 5 ppm by weight (relative to a basic compound exclusive of a solvent); and then polymerizing a resultant neutralized product, the acrylic acid composition including: (i) a methoxyphenol content of 10 to 200 ppm by weight relative to the weight of acrylic acid; and (ii) at least one compound content of which is 0 to 10 ppm by weight relative to the weight of acrylic acid, the compound being selected from the group consisting of protoanemonin and furfural.

22 Claims, No Drawings

(56) References Cited

FOREIGN PATENT DOCUMENTS

| | | |
|---|---|---|
| JP | 2001-040013 | 2/2001 |
| JP | 2001-040014 | 2/2001 |
| JP | 2003-246810 | 9/2003 |
| JP | 2005-054050 | 3/2005 |
| JP | 2008-534695 | 8/2008 |
| RU | 2 106 153 | 3/1998 |
| TW | 228528 | 8/1994 |
| TW | 399062 | 7/2000 |
| TW | 422866 | 2/2001 |
| TW | 432092 | 5/2001 |
| WO | WO 98/52979 | 11/1998 |
| WO | WO 01/98382 A1 | 12/2001 |
| WO | WO 03/014172 A2 | 2/2003 |
| WO | WO 03/051940 A1 * | 3/2003 |
| WO | WO 03/051940 | 6/2003 |
| WO | WO-03078378 A1 | 9/2003 |
| WO | WO 03/095510 A1 | 11/2003 |
| WO | WO-2004003036 A1 | 1/2004 |
| WO | WO 2004/052819 A2 | 6/2004 |
| WO | WO 2004/052949 A1 | 6/2004 |
| WO | WO 2004/061010 A1 * | 7/2004 |
| WO | WO-2004069404 A1 | 8/2004 |

OTHER PUBLICATIONS http://www.home-water-purifiers-and-filters.com/carbon-water-filter.php, 2011.*

BASF Acrylic Acid Glacial, Technical Data Sheet, Mar. 2001.*

Database WPI Week 200454, Thomson Scientific, London, GB, AN 2004-561593, XP0002555199, 2004.

European Search Report mailed Dec. 2, 2009, EP 06 73 1728.

Chinese Office Action and English translation thereof, Jul. 2009, 200680011103.1.

Russian Decision to Grant English translation thereof, Nov. 2008, 2007141544/04 (045482).

European Search Report dated Dec. 1, 2009 for European Patent Application No. 06731732.1.

Russian Decision to Grant dated Aug. 14, 2009 for Russian patent application No. 2007140959 with English translation.

State Intellectual Property Office of the P.R. China Examination Report dated Jan. 20, 2009.

Korean Office Action together with its English translation for Korean Patent Application No. 10-2007-7022676 (2008).

The Polymer Handbook, 3rd Edition, p. 524 and p. 527-539.

Office Action dated Dec. 17, 2013 issued in U.S. Appl. No. 11/883,929.

Notice of Opposition dated Oct. 28, 2013 issued in European Application No. 06731728.9.

Ullmann's Encyclopedia of Industrial Chemistry (2003, Bd 33:S. 241-242, Bd.8:S. 247-248).

Office Action dated Sep. 14, 2009 issued in U.S. Appl. No. 11/883,929.

Office Action dated Mar. 18, 2010 issued in U.S. Appl. No. 11/883,929.

Office Action dated Aug. 31, 2010 issued in U.S. Appl. No. 11/883,929.

* cited by examiner

PRODUCTION PROCESS OF POLYACRYLIC ACID (SALT) WATER-ABSORBENT RESIN

TECHNICAL FIELD

The present invention relates to a polyacrylic acid (salt) water-absorbent resin, a production process thereof, and acrylic acid used in polymerization for production of a water-absorbent resin. More specifically, the present invention particularly relates to a water-absorbent resin having improved relationship between absorption capacity and water-soluble polymer, which are conflicting properties of the water-absorbent resin.

BACKGROUND ART

In recent years, water-absorbent resins having a high water absorbency are developed and frequently used mainly for disposable uses, for example, as absorbent articles (e.g. disposable diapers and sanitary napkins) and further as water-retaining agents for agriculture and horticulture and for industrial sealing materials. As to such water-absorbent resins, many monomers and hydrophilic polymers are proposed as their raw materials. Of them, acrylic water-absorbent resins as obtained from acrylic acid and/or its salt as the monomers are industrially most commonly used because of their high water absorbency.

Because water-absorbent resins are generally used for disposable uses (such as disposable diapers), it is essential that they are inexpensive. Therefore, the enhancement of their productivity is in high demand. In addition, there is a natural high demand for the absorbent articles to avoid problems with respect to the safety and coloration of the absorbent articles. Specifically, the water-absorbent resin contains the unreacted residue of acrylic acid. Although the content of the unreacted acrylic acid is several hundred to about 1000 ppm by weight, a decrease in the content of the unreacted acrylic acid is demanded. In addition, the water-absorbent resin is combined with white pulp in the absorbent articles. Therefore there is a high demand for the water-absorbent resin also to be white so as not to give any foreign-substance feeling or appearance caused by coloration.

In addition, the water-absorbent resin is water-swellable and water-insoluble. However, as described in Patent Document 1, in the water-absorbent resin, there is also contained an uncrosslinked water-soluble polymer (water-soluble component) in the range of several wt % to several tens of wt %. The decrease of the content of this water-soluble component is also demanded. Moreover, as described in Patent Document 2, the absorbent articles containing the water-absorbent resin is required to possess acceptable water absorption properties under pressure, such as absorption capacity under pressure and liquid permeation quantity under pressure.

In order to solve the above problem, there has been suggested the process including the step of polymerizing a monomer having impurities in small amounts to produce a water-absorbent resin. Examples of such a process include: the process including the step of carrying out purification so that a monomer has a heavy metal content of not more than 0.1 ppm and the step of carrying out polymerization of the monomer (Patent document 3); the process including the step of carrying out polymerization by using acrylic acid including acrylic dimer or oligomer in small amounts (Patent documents 4 and 5); the process including the step of carrying out purification of acrylic acid for polymerization to obtain an acetic acid or proprionic acid content of less than 400 ppm (Patent document 6); the process including the step of carrying out polymerization by using acrylic acid including protoanemonin in small amounts (Patent document 7); the process including the step of carrying out polymerization by using acrylic acid including furfural in small amounts (Patent document 8); and the process including the step of carrying out polymerization by using acrylic acid including hydroquinone in small amounts (Patent document 9). As the process including the step of reducing the amount of impurities in material for a water-absorbent resin, the following processes have been suggested. That is, the process including the step of treating acrylic acid with an aldehyde treatment agent (Patent document 10), and the process including the step of treating acrylate with an active carbon (Patent document 11).

As disclosed in Patent documents 3 through 11, there has been suggested the method for realizing a water-absorbent resin with excellent properties by the process including the step of purifying acrylic acid or the like as raw material at a high purity. However, there occurs the cost problem and the problem of decrease in productivity.

Furthermore, there has been suggested the polymerization process for a water-absorbent resin, including the step of adding trace components in certain amounts for the improvement in properties of the resulting water-absorbent resin. Examples thereof includes: the process in which acrylic acid has a methoxyphenol content of 10 to 200 ppm (Patent document 12); the process in which there coexists furfural of 11 to 2000 ppm (Patent document 13); and the process using metal (Patent documents 14 and 15). However, in Patent documents 12 and 13, there occurs the problem that the resultant water-absorbent resin becomes colored (turns yellow) due to oxidation of methoxyphenol and furfural, which are contained in a monomer, in the course of the production of a water-absorbent resin.

[Patent document 1]
U.S. Pat. No. 4,654,039
[Patent document 2]
U.S. Pat. No. 5,562,646
[Patent document 3]
Japanese Unexamined Patent Publication No. 31306/1991 (Tokukaihei 3-31306),
[Patent document 4]
Japanese Unexamined Patent Publication No. 211934/1994 (Tokukaihei 6-211934)
[Patent document 5]
International Publication WO04/52949
[Patent document 6]
International Publication WO03/95510
[Patent document 7]
European Patent No. 1302485
[Patent document 8]
U.S. Patent Application Publication No. 2004/0110913
[Patent document 9]
U.S. Pat. No. 6,444,744
[Patent document 10]
International Publication WO03/14172
[Patent document 11]
International Publication WO04/52819
[Patent document 12]
U.S. Patent Application Publication No. 2004/0110914
[Patent document 13]
U.S. Patent Application Publication No. 2004/0110897
[Patent document 14]
U.S. Pat. No. 5,439,993
[Patent document 15]
European Patent No. 1457541

DISCLOSURE OF INVENTION

An object of the present invention is to provide a process for producing a water-absorbent resin having an improved relationship between absorption capacity and water-soluble polymer, which are conflicting properties of a water-absorbent resin, being mildly controlled for polymerization reaction, maintaining and improving high absorption properties, being of no odor, being uncolored water-absorbent resin odor, and being produced with a high productivity.

In order to solve the problem, as a result of extensive research, the inventors of the present invention have found that the problem can be solved by producing a water-absorbent resin by using (i) an acrylic acid containing particular trace components and (ii) a basic compound having an iron content of 0.2 to 5 ppm by weight, and have completed the present invention.

More specifically, a first water-absorbent resin production process is a process for producing a water-absorbent resin by polymerizing an acrylic acid composition including acrylic acid and/or its salt, the process comprising (a) the step of neutralizing the acrylic acid composition with a basic composition; and then polymerizing a resultant neutralized product, thereby forming a hydrogel crosslinked polymer, the acrylic acid composition including: (i) a methoxyphenol content of 10 to 200 ppm by weight relative to the weight of acrylic acid; and (ii) at least one compound content of which is 0 to 10 ppm by weight relative to the weight of acrylic acid, the compound being selected from the group consisting of protoanemonin and furfural, the basic composition including a basic compound and iron, the basic composition having an iron content of 0.2 to 5.0 ppm by weight in terms of $Fe_2O_3$.

A second water-absorbent resin production process is a process for producing a water-absorbent resin by polymerizing an acrylic acid composition including acrylic acid and/or its salt, the process comprising (a') the step of polymerizing the acrylic acid composition to thereby form a hydrogel crosslinked polymer; and neutralizing the hydrogel crosslinked polymer with a basic composition, the acrylic acid composition including: (i) a methoxyphenol content of 10 to 200 ppm by weight relative to the weight of acrylic acid; and (ii) at least one compound content of which is 0 to 10 ppm by weight relative to the weight of acrylic acid, the compound being selected from the group consisting of protoanemonin and furfural, the basic composition including a basic compound and iron, the basic composition having an iron content of 0.2 to 5.0 ppm by weight in terms of $Fe_2O_3$.

The above arrangement makes it possible to produce, with a high productivity, a water-absorbent resin having an improved relationship between absorption capacity and water-soluble polymer which are conflicting properties of the water-absorbent resin, being easily controlled for polymerization reaction, being of no odor, being less colored, and being of high absorption properties.

The first and second water-absorbent resin production processes preferably further include, after the step (a) or the step (a'), (b) the step of drying the hydrogel crosslinked polymer by application of heat and (c) the step of subjecting the resultant hydrogel crosslinked polymer to surface cross-linking treatment by application of heat.

The basic compound is preferably alkaline-metal hydroxide or alkaline-metal carbonate, more preferably sodium hydroxide or sodium carbonate.

The acrylic acid composition preferably has an unpolymerizable organic compound content of 1 to 1000 ppm by weight, wherein the unpolymerizable organic compound has a solubility parameter of $(1.0$ to $2.5)\times10^4$ $(Jm^{-3})^{1/2}$.

Further, the first and second water-absorbent resin production processes are preferably such that a chelating agent is added to the acrylic acid composition or the hydrogel crosslinked polymer.

Still further, the iron is preferably $Fe_2O_3$.

Yet further, the acrylic acid composition preferably has: (I) a phenothiazine content of 0 to 0.1 ppm by weight relative to the weight of acrylic acid; (II) at least one compound content of which is 0 to 5 ppm by weight relative to the weight of acrylic acid, the compound being selected from the group consisting of aldehyde, except furfural, and maleic acid; and (III) at least one saturated carboxylic acid content of which is 10 to 800 ppm by weight relative to the weight of acrylic acid, the saturated carboxylic acid being selected from the group consisting of acetic acid and propionic acid.

BEST MODE FOR CARRYING OUT THE INVENTION

The "crosslinked water-absorbent resin" in the present invention refers to a polymer having water-swellability and water-insolubility as a result of introducing a crosslinked structure into the polymer, wherein the "water-swellability" means physiological saline absorbency (GVs) without pressure of at least 2 times, preferably 5 to 200 times, more preferably 20 to 100 times, and wherein the "water-insolubility" means substantial water-insolubility such that the water-soluble polymer content in the resin is essentially 0 to 50 wt %, preferably 0 to 25 wt %, more preferably 0 to 15 wt %, still more preferably 0 to 10 wt %. These properties are measured by methods defined in an example below.

A polyacrylic acid(salt) water-absorbent resin in the present invention is the one obtained by polymerizing a monomer including acrylic acid and/or its salt as a main component, wherein the acrylic acid and/or its salt is in a total amount of essentially 50 to 100 mol %, more preferably 70 to 100 mol %, still more preferably 90 to 100 mol %, particularly preferably substantially 100 mol %, relative to the entire monomers (exclusive of cross-linking agents). Note that, the term "monomer" herein refers to a monomer including acrylic acid and/or its salt as a main component, and is also used as a synonym for "acrylic acid component".

In terms of the properties, the acrylate used in the present invention is: preferably monovalent salts of acrylic acid, such as alkaline metal salts, ammonium salts, and amine salts; more preferably alkaline metal acrylates; and still more preferably alkaline metal acrylates selected from among sodium salt, lithium salt, and potassium salt. Further, polyvalent metal salts, such as calcium salts and aluminum salts, may be used in combination as long as the water-absorbent resin as obtained in the present invention has water-swellability.

The water-absorbent resin, as obtained in the present invention, is such that 20 to 99 mol %, preferably 50 to 95 mol %, more favorably 60 to 90 mol %, in terms of neutralization ratio, of the acid groups of the polymer are neutralized. The neutralization may be carried out either to the monomer component, i.e. acrylic acid composition before polymerization, or to the polymer, e.g. hydrogel crosslinked polymer during and/or after polymerization. Furthermore, the neutralization of the monomer component and the neutralization of the polymer may be adopted in combination. However, it is preferable to subject acrylic acid as the monomer component, i.e. acrylic acid included in the acrylic acid composition, to alkali treatment as will be hereinafter described.

(2) Unpolymerizable Organic Compound

The unpolymerizable organic compound is an organic compound having no polymerizable unsaturated bond formed with a vinyl group, an allyl group, or the like, and the present invention preferably uses a monomer including an unpolymerizable organic compound content of 1 to 1000 ppm by weight, wherein the unpolymerizable organic compound has a solubility parameter of $(1.0$ to $2.5)\times10^4$ $(Jm^{-3})^{1/2}$. In other words, the acrylic acid composition of the present invention preferably include an unpolymerizable organic compound content of 1 to 1000 ppm by weight, wherein the unpolymerizable organic compound has a solubility parameter of $(1.0$ to $2.5)\times10^4$ $(Jm^{-3})^{1/2}$. Note that, the unpolymerizable organic compound in the present invention is an organic compound with no polymerizable unsaturated bonds. Such an organic compound is (i) a compound having saturated bonds and being unpolymerizable by radical polymerization, ultraviolet polymerization, or gamma-ray polymerization by thermal decomposition or an oxidizing agent/reducing agent, or (ii) an organic compound such as an aromatic compound.

The solubility parameter (δ) is herein a cohesive energy density and can be calculated from the following equation:

$$\delta((Jm^{-3})^{1/2}) = \rho \Sigma G/M$$

where ρ is density (g/cm$^3$), G is the Holly cohesive energy constant, ΣG is a sum of cohesive energy constants of component atom groups, ρ and G are values at a temperature of 25±1° C., and M is molecular weight.

In the present invention, if the solubility parameter δ is calculated in the unit ((calm$^{-3}$)$^{1/2}$), the solubility parameter δ is appropriately expressed in the unit (Jm$^{-3}$)$^{1/2}$.

The present invention uses the monomer including the above particular compound in certain amounts, thereby producing, with a high productivity, a water-absorbent resin having (i) an improved relationship between absorption capacity and water-soluble polymer which are conflicting properties of the water-absorbent resin, (ii) being easily controlled for polymerization reaction, (iii) being less colored, and (iv) being of high absorption properties. A monomer having an unpolymerizable organic compound content of less than 1 ppm by weight, wherein the unpolymerizale organic compound has a solubility parameter of (1.0 to 2.5)×10$^4$ (Jm$^{-3}$)$^{1/2}$, is not preferred because it has the difficulty in being controlled for polymerization, which is caused by an excessive rise in temperature of a polymerized substance due to heat liberated by the polymerization, and causes degradation in absorption properties. Meanwhile, a monomer having an unpolymerizable organic compound content of more than 1000 ppm by weight, wherein the unpolymerizale organic compound has a solubility parameter of (1.0 to 2.5)×10$^4$ (Jm$^{-3}$)$^{1/2}$, includes too much amount of the unpolymerizable organic compound to achieve the object of the present invention, and might cause the problem, e.g. odor from a resultant water-absorbent resin.

Thus, such an unpolymerizable organic compound is used in an amount of 1 to 10000 ppm by weight, preferably 1 to 500 ppm by weight, more preferably 1 to 300 ppm by weight, still more preferably 5 to 300 ppm by weight, particularly preferably, 10 to 300 ppm by weight, most preferably 10 to 100 ppm by weight, relative to the monomer (acrylic acid composition).

Further, the particular compound (unpolymerizable organic compound) is finally removed by a particular heating step (e.g. drying and surface treatment) as will be described hereinafter, so that the resultant water-absorbent resin is free from odors and other problems.

The solubility parameter of the unpolymerizable organic compound is normally (1.0 to 2.5)×10$^4$ (Jm$^{-3}$)$^{1/2}$, preferably (1.0 to 2.2)×10$^4$ (Jm$^{-3}$)$^{1/2}$, more preferably (1.1 to 2.0)×10$^4$ (Jm$^{-3}$)$^{1/2}$, still more preferably 1.3 to 2.0)×10$^4$ (Jm$^{-3}$)$^{1/2}$, and most preferably (1.5 to 1.9)×10$^4$ (Jm$^{-3}$)$^{1/2}$.

More specifically, the unpolymerizable organic compound is at least one compound selected from among heptane (boiling point: 95° C.), dimethyl cyclohexane (boiling point: 132° C.), ethyl cyclohexane, toluene (boiling point: 110° C.), ethylbenzene (boiling point: 136° C.), xylene (boiling point: 138 to 144° C.), diethyl ketone (boiling point: 101° C.), diisopropyl ketone (boiling point: 124 to 125° C.), methyl propyl ketone (boiling point: 102° C.), methyl isobutyl ketone, methyl t-butyl ketone, n-propyl acetate (boiling point: 101° C.), n-butyl acetate (boiling point: 124 to 125° C.), diphenyl ether (boiling point: 259° C.), and diphenyl (boiling point: 255° C.). Of these unpolymerizable organic compounds, aromatic compounds are preferable, and toluene, diphenyl ether, and diphenyl are particularly preferable in terms of polymerization properties and productivity.

The organic compound having a solubility parameter of (1.0 to 2.5)×10$^4$ (Jm$^{-3}$)$^{1/2}$, which is an organic compound having an excellent compatibility with acrylic acid and having no polymerizable unsaturated bonds, refers to a lipophilic organic compound. Of such unpolymerizable organic compounds, an organic compound of no halogen content is preferable, and hydrocarbon consisting of only carbon and hydrogen is more preferable, in terms of environmental loads. Further, a boiling point of the unpolymerizable organic compound is preferably 95 to 300° C., more preferably 130 to 260° C. The organic compound having a solubility parameter of more than 2.5×10$^4$ (Jm$^{-3}$)$^{1/2}$ is not preferable in terms of polymerization control and polymerization reaction.

The unpolymerizable organic compound is preferably included in a monomer (acrylic acid composition) before polymerization. The monomer including unpolymerizable organic compound may be prepared such that the unpolymerizable organic compound is added to a monomer, i.e. an aqueous solution of acrylic acid composition after the preparation of the monomer, the unpolymerizable organic compound is added to a monomer i.e. an aqueous solution of acrylic acid composition during the preparation of the monomer, or the unpolymerizable organic compound is included in advance or added to raw materials for a monomer, i.e. components of acrylic acid composition including acrylic acid, cross-linking agents, water, and alkali compounds. In such preparation methods, the unpolymerizable organic compound is hydrophobic and generally water-insoluble, and therefore is preferably dissolved or included in acrylic acid, in advance. In the present invention, it is preferable that the unpolymerizable organic compound is included or added, in advance, to acrylic acid as used in preparing the monomer. That is, it is preferable that the unpolymerizable organic compound is dissolved in advance in an unneutralized acrylic acid so that the unneutralized acrylic acid is used for the preparation of an aqueous solution of the monomer.

(3) Acrylic Acid Used in Polymerization for Production of a Water-Absorbent Resin and Acrylic Acid Composition Examples of known industrial processes for producing acrylic acid include a process of catalytic gas phase oxidation of propylene and/or acrolein, an ethylene cyanohydrin process, a high pressure Reppe process, an improved Reppe process, a ketene process, and an acrylonitrile hydrolysis process. Of them, the process of catalytic gas phase oxidation of propylene and/or acrolein is most commonly employed. Then, in the present invention, acrylic acid as obtained by such a catalytic gas phase oxidation process is preferably used. This acrylic acid, as obtained by the catalytic gas phase oxidation process, usually contains impurities in an amount of not less than approximately 2000 ppm by weight. Such an acrylic acid including the impurities can be herein referred to as an acrylic acid composition.

In one of the processes for producing a water-absorbent resin according to the present invention, used is the acrylic acid composition preferably including the unpolymerizable organic compound of 1 to 1000 ppm by weight, in addition to acrylic acid. Preferably, the acrylic acid composition further includes β-hydroxypropionic acid and/or acrylic acid dimer in total amounts of 1 to 1000 ppm by weight (based on the weight in terms of the unneutralized acrylic acid; hereinafter omitted), preferably 1 to 500 ppm by weight, more preferably 1 to 300 ppm by weight, and also includes methoxyphenol of 10 to 200 ppm by weight.

Specific examples of the aforementioned methoxyphenol include o-, m-, p-methoxyphenol and methoxyphenol which have at least one substituent such as methyl, t-butyl, or hydroxyl. In the present invention, p-methoxyphenol is particularly preferable. A methoxyphenol content is 10 to 200 ppm by weight, preferably in the range of 10 to 100 ppm by weight, more preferably in the range of 10 to 90 ppm by weight, still more preferably in the range of 10 to 80 ppm by weight, most preferably in the range of 10 to 70 ppm by weight. In the case where a p-methoxyphenol content is more than 200 ppm by weight, there occurs a problem that the resultant water-absorbent resin becomes colored (becomes tinged with yellow/turns yellow). On the other hand, in the case where the p-methoxyphenol content is less than 10 ppm by weight, particularly less than 5 ppm by weight, in other words, in the case where the p-methoxyphenol which is a polymerization inhibitor has been removed by purification such as distillation, not only is there a danger that the polymerization will take place before intentionally being initiated, but also, surprisingly, the polymerization rate rather becomes slow.

The (i) unpolymerizable organic compound and (ii) β-hydroxypropionic acid and/or acrylic acid dimer included in total amounts of less than 1 ppm by weight make it difficult to control for polymerization, which is caused by an excessive rise in temperature of a polymerized substance due to heat liberated by the polymerization, and causes degradation in absorption properties. The (i) unpolymerizable organic compound and (ii) β-hydroxypropionic acid and/or acrylic acid dimer included in too much total amounts causes the increase of a residual monomer content (residual acrylic acid) in the water-absorbent resin.

Apart from the methoxyphenol, other polymerization inhibitors can be used in the acrylic acid composition as used in the production process of the present invention. For example, phenothiazine, hydroquinone, copper salts, and Methylene Blue are effective polymerization inhibitors. However, such polymerization inhibitors impair the polymerization, unlike the methoxyphenol. Such polymerization inhibitors in a lower content are preferred, and the content of the polymerization inhibitors is preferably 0 to 0.1 ppm by weight, more preferably 0 ppm by weight (which is lower than a detection limit).

The acrylic acid composition as used in the production process of the present invention may have a protoanemonin and/or furfural content. As the protoanemonin and/or furfural content increases, not only does the polymerization time (time elapsed until the polymerization temperature reaches its peak) become longer to increase the residual monomer content, but also the water-soluble component content increases much more than the small increase in the absorption capacity, resulting in relative deterioration of properties. From the viewpoint of the enhancements of the properties and performances of the resultant water-absorbent resin, the protoanemonin and/or furfural content of the acrylic acid composition is preferably in the range of 0 to 20 ppm by weight. More specifically, the protoanemonin and/or furfural content of the acrylic acid composition is preferably not more than 10 ppm by weight, more preferably in the range of 0.01 to 5 ppm by weight, still more preferably 0.05 to 2 ppm by weight, particularly preferably 0.1 to 1 ppm by weight.

Further, the acrylic acid composition as used in the production process of the present invention is preferably lower in aldehyde, except furfural, and/or maleic acid content. The aldehyde and/or maleic acid content is preferably 0 to 5 ppm by weight, more preferably 0 to 3 ppm by weight, still more preferably 0 to 1 ppm by weight, particularly preferably 0 ppm by weight (which is lower than a detection limit), relative to the weight of acrylic acid. Examples of aldehyde except furfural include benzoic aldehyde, acrolein, and acetaldehyde.

Still further, the acrylic acid composition as used in the production process of the present invention includes a saturated carboxylic acid consisting of acetic acid and/or propionic acid. A saturated carboxylic acid content is preferably not more than 1000 ppm by weight, more preferably 10 to 800 ppm by weight, particularly preferably 100 to 500 ppm by weight, relative to the weight of acrylic acid. The saturated carboxylic acid is unpolymerizable and volatile. As such, the saturated carboxylic acid content of more than 1000 ppm by weight causes the odor problem. However, a low saturated carboxylic acid content is preferable because it causes the resultant water-absorbent resin to have a safe antibacterial activity.

In the present invention, examples of the process for obtaining the aforementioned acrylic acid composition, but are not limited to, include the following processes (A) to (D). The quantification of the components included in the acrylic acid composition can be carried out by liquid chromatography or gas chromatography.

Process (A): A process including the step of distilling commercially available acrylic acid containing p-methoxyphenol as a polymerization inhibitor in an amount of not less than 200 ppm by weight or an aqueous solution of this acrylic acid, thereby adjusting the methoxyphenol (e.g. p-methoxyphenol (boiling point: 113 to 115° C./5 mmHg)) content to the above-specified content.

Process (B): A process including the step of adding methoxyphenol as a polymerization inhibitor to acrylic acid initially containing no methoxyphenol, such as p-methoxyphenol, or to an aqueous solution of this acrylic acid.

Process (C): A process including the step of adjusting the methoxyphenol (p-methoxyphenol) content to the content as defined in the present invention, in the course of the process for producing acrylic acid.

Process (D): A process including the step of blending acrylic acids having different methoxyphenol (e.g. p-methoxyphenol) contents, thereby adjusting the methoxyphenol content to the content as defined in the present invention.

In the processes (A) through (D), an unpolymerizable organic compound having a solubility parameter of 3 to 5 $(Jcm^3)^{1/2}$ in the acrylic acid (boiling point: 139° C.) in the above-specified amounts, and β-hydroxypropionic acid and/or acrylic acid dimer in the above-specified amounts may be prepared concurrently.

Specific examples of the process for obtaining the acrylic acid composition (also referred to as acrylic acid having trace components as impurities) in the process (A), include processes involving distillation, crystallization, or adsorption by ion-exchange resins. Hereinafter, examples of the process involving the distillation and crystallization are described.

A process including the steps of: distilling the commercially available acrylic acid with a distillation column having a condenser, a distillate-extracting tube, and a reflux-supplying tube at a top portion of the column and further having a boiler and a raw-material-liquid-supplying tube at a lower portion of the column and still further having a stabilizing-agent-supplying tube at an upper portion of the condenser; and, while adding methoxyphenol from the stabilizing-agent-supplying tube, obtaining the acrylic acid composition including methoxyphenol in a predetermined content.

A process including the step of introducing the commercially available acrylic acid into a crystallizer, thereby obtaining the acrylic acid composition including methoxyphenol in a predetermined content.

How to add methoxyphenol during the distillation in the former process above is not particularly limited. The methoxyphenol may be added either directly in the form of a powder, or in the form of a solution in the acrylic acid. Suitable devices that can be used in the latter process above are disclosed in Japanese Examined Patent Publication No. 41637/1978 (Tokukousho 53-41637).

There are also known techniques involving removal of impurities, such as polymerization inhibitors and acrylic acid dimer, by purification of acrylic acid (acrylic acid containing trace components as impurities) in preparation for polymerization in producing the water-absorbent resin (Japanese Unexamined Patent Publication No. 211934/1994, Japanese Unexamined Patent Publication No. 31306/1.991, European Patent No. 0942014, and European Patent No. 0574260). However, in the case where acrylic acid is distilled in preparation for its polymerization, the p-methoxyphenol content of acrylic acid is substantially ND (Non-Detectable/detection limit 1 ppm by weight/quantified with UV) after the distillation due to the difference between boiling points of acrylic acid and p-methoxyphenol. Accordingly, even if techniques as conventionally carried out for purifying acrylic acid are applied to the commercially available acrylic acids having a p-methoxyphenol content of more than 200 ppm by weight, it is impossible or extremely difficult to adjust the p-methoxyphenol content into the specific range of 10 to 200 ppm by weight. For such an adjustment, it is necessary to intentionally carry out the process like the above processes (A) through (D).

(4) Basic Composition

"Basic composition" herein means a composition containing a basic compound. In the present invention, the basic composition preferably contains iron as will be described hereinafter, i.e. iron-containing compound, as well as the basic compound.

Examples of the basic compound as used in the present invention include alkaline-metal (hydrogen)carbonate, alkaline-metal hydroxides, ammonia, and organic amines. However, in order to obtain a water-absorbent resin having still higher properties, strong-alkali substances i.e. alkaline-metal hydroxides such as sodium hydroxide, potassium hydroxide, and lithium hydroxide are preferable. Among the alkaline-metal hydroxides listed above, sodium hydroxide is particularly preferred. Sodium hydroxide usually has a sodium carbonate and/or sodium chloride content of about 0 to 5%. Such a sodium hydroxide is also applied preferably to the present invention.

As described in Patent document 3, it has been known that a heavy metal content of more than 0.1 ppm by weight in an aqueous solution of a monomer increases a residual monomer content in a water-absorbent resin. On the contrary, according to the process of the present invention, i.e. the process including the step of preparing a monomer by using (i) acrylic acid containing particular trace components and (ii) a basic composition containing iron in particular amounts (0.2 to 5 ppm by weight) (based on the weight in terms of $Fe_2O_3$) (Preferably, a basic composition containing iron and caustic soda), it was found out that the process of the present invention realized shortening of a polymerization time, reduction in water-soluble component content, and a less colored water-absorbent resin.

Further, Patent document 3 discloses distillation of acrylic acid and activated carbon treatment of caustic soda, as the techniques for decreasing the heavy metal content to 0.1 ppm by weight, preferably not more than 0.02 ppm by weight. However, Patent document 3 does not disclose methoxyphenol as used in the present invention. Even if the acrylic acid of Patent document 3 has a methoxyphenol content of not less than 200 ppm by weight, methoxyphenol having a high boiling point (p-methoxyphenol has a boiling point of 113 to 115° C./5 mmHg) is removed by distillation and purification of the acrylic acid (boiling point: 139° C.) as described in Patent document 3. As a result of this, a methoxyphenol content in the distillated acrylic acid becomes substantially 0 ppm by weight (lower than the detection limit). In addition, Patent document 3 is totally silent about effectiveness of heavy metal for the polymerization in the process for producing a water-absorbent resin.

More specifically, a basic composition as used in the present invention contains a basic compound and iron. The basic composition has essentially a iron content (based on the weight in terms of $Fe_2O_3$) in the range of 0.01 to 10.0 ppm by weight, preferably in the range of 0.2 to 5.0 ppm by weight, and more preferably in the range of 0.5 to 5.0 ppm by weight, relative to solids content of the basic composition. The iron content of lower than 0.01 ppm by weight causes not only the risk that the polymerization can possibly take place before the addition of a polymerization initiator, but also the possibility of a slow polymerization even with the polymerization initiator added. The iron as used in the present invention may be Fe ion; however, it is preferably trivalent iron in terms of effectiveness, particularly preferably $Fe_2O_3$.

In the present invention, examples of the method for obtaining a basic composition having an iron content of 0.01 to 10.0 ppm by weight, which are not limited to, include the following methods (A) and (B):

Method (A): A method of selecting, from among commercially available basic compounds, a basic compound having an iron-containing compound content of 0.01 to 10.0 ppm by weight (based on the weight in terms of $Fe_2O_3$); and Method (B): A method of removing or reducing iron from a basic compound having an iron-containing compound content of not less than 10.0 ppm by weight (based on the weight in terms of $Fe_2O_3$), by using an activated carbon, a chelate-ion exchange resin, a chelating agent, or the like, and thereafter adjusting the basic compound so as to have an iron content in the range of 0.01 to 10.0 ppm by weight by adding iron thereto.

In the present invention, if the addition of iron such as $Fe_2O_3$ is necessary, the iron may be added to either a monomer, i.e. an acrylic acid composition, or a basic composition.

(5) Subjecting an Acrylic Acid to Alkali Treatment

The process for producing a water-absorbent resin, according to the present invention, includes the step of preparing the monomer component from the aforementioned acrylic acid containing trace components. In the step, it is preferable to neutralize the acrylic acid with the basic composition by subjecting the acrylic acid to alkali treatment with the aforementioned basic composition. For example, it is preferable to neutralize the acrylic acid composition with the basic composition.

The alkali treatment, as referred to in the present invention, means a treatment in which the acrylic acid to be treated is subjected to neutralization at a temperature not lower than a certain temperature (high-temperature neutralization) or neutralization at a neutralization ratio not lower than a certain neutralization ratio (high neutralization). Such an alkali treatment greatly promotes the polymerization of acrylic acid. Specific examples thereof include: a process in which the acrylic acid composition is gradually added to a certain amount of basic composition to get a strong alkaline region; and a process in which the alkali treatment is carried out simultaneously with the neutralization by line-mixing the acrylic acid composition and a strong-alkali basic composition together.

As to the high-temperature neutralization, the temperature in the alkali treatment is higher than a temperature in normal neutralization. More specifically, the temperature in the alkali treatment is preferably in the range of 30° C. to the boiling point, more preferably in the range of 40° C. to the boiling point, still more preferably in the range of 50° C. to the boiling point, particularly preferably in the range of 60° C. to the boiling point. In the alkali treatment, in cases where the temperature is low and where no strong alkali is used and further where the neutralization has not yet been completed, the polymerizability is so low that inferior results may be also obtained with regard to the properties even if a purified acrylic acid is used.

As to the high neutralization, these alkali treatments are preferably in the presence of an excess of alkali so that the neutralization ratio of acrylic acid is substantially 100 mol %. The amount of alkali can be more than is necessary to neutralize 100 mol % of the acrylic acid.

Examples of the basic compound contained in the basic composition as used for the neutralization include alkaline-metal hydroxides such as sodium hydroxide, potassium hydroxide, and lithium hydroxide. Among the alkaline-metal hydroxides listed above, sodium hydroxide is particularly preferred. In the alkali treatment, particularly, strong-alkali treatment, the acrylic acid is treated in such a manner to form an aqueous solution or dispersion including post-neutralization acrylate, concentration of which is preferably 10 to 80 wt %, more preferably 20 to 60 wt %, still more preferably 30 to 50 wt %. The time of such an alkali treatment, particularly the treatment time in the case of carrying out the alkali treatment in the presence of an excess of the alkali, is appropriately determined in the range of preferably 1 second to 2 hours, more preferably 5 seconds to 1 hour.

Furthermore, the alkali treatment is carried out in the presence of oxygen for stability. Preferably, the alkali treatment is carried out in a state where the aqueous acrylic acid (or salt) solution, i.e. an aqueous solution of acrylic acid composition, contains oxygen preferably in the range of 0.5 to 20 ppm, more preferably 1 to 15 ppm, still more preferably 1.5 to 10 ppm. In the case where the oxygen content is low, there are problems of the stability of the monomer in the alkali treatment. The alkali treatment is preferably carried out under an oxygen or air atmosphere, more preferably, while oxygen or air is blown in and/or drawn in. The oxygen content is measurable with a dissolved oxygen meter (e.g. membrane-type polarograph). The monomer thus obtained has preferably a turbidity (specified by JIS K-0101) of not more than 0.5.

(6) Another Monomer

The monomer includes acrylic acid and/or its salt in the range as previously defined. Such a monomer may be used with another monomer in combination. In other words, in the present invention, the acrylic acid composition may contain acrylic acid and/or its salt in the aforementioned range and also contain another monomer.

Examples of this monomer that can be used in combination include monomers as disclosed in U.S. patents and European patents as will be described later. Specific examples thereof further include copolymers as obtained by copolymerizing the acrylic acid and/or its salt with, for example, water-soluble or hydrophobic unsaturated monomers such as methacrylic acid, (anhydrous) maleic acid, fumaric acid, crotonic acid, itaconic acid, vinylsulfonic acid, 2-(meth)acrylamido-2-methylpropanesulfonic acid, (meth)acryloxyalkane-sulfonic acid, and their alkaline metal salts and ammonium salts, and further, N-vinyl-2-pyrrolidone, N-vinylacetamide, (meth)acrylamide, N-isopropyl(meth)acrylamide N,N-dimethyl(meth)acrylamide, 2-hydroxyethyl (meth)acrylate, methoxypolyethylene glycol (meth)acrylate, polyethylene glycol (meth)acrylate, isobutylene, and lauryl (meth)acrylate.

The crosslinking method as used in the present invention is not especially limited, but examples thereof include: (A) a method which involves the step of adding a cross-linking agent during and/or after the polymerization, thereby post-crosslinking; (B) a method which involves radical crosslinking with radical polymerization initiators; and (C) a method which involves radiation crosslinking such as by electron beams. However, a preferable one is (D) a method which involves the steps of beforehand adding a predetermined amount of internal cross-linking agent to a monomer, and then carrying out polymerization simultaneously with and/or after which a crosslinking reaction is carried out.

Examples of the internal cross-linking agent as used in the present invention include N,N'-methylenebisacrylamide, (poly)ethylene glycol di(meth)acrylate, (poly)propylene glycol di(meth)acrylate, (polyoxyethylene) trimethylolpropane tri(meth)acrylate, trimethylolpropane di(meth)acrylate, polyethylene glycol di(β-acryloyloxypropionate), trimethylolpropane tri(β-acryloyloxypropionate), poly(meth)allyloxyalkanes, polyethylene glycol diglycidyl ether, ethylene glycol, polyethylene glycol, and glycerol. These internal-crosslinking agents may be used either alone or in combinations with each other. Incidentally, when at least one internal-crosslinking agent is used, it is favorable in consideration of, for example, the absorption properties of the resultant water-absorbent resin that a compound with at least two polymerizable unsaturated groups as an essential component is used during the polymerization.

The amount of the above internal cross-linking agent is preferably in the range of 0.005 to 2 mol %, more preferably 0.01 to 1 mol %, still more preferably 0.05 to 0.2 mol %, relative to the aforementioned monomer. In the case where the amount of the above cross-linking agent used is smaller than 0.005 mol % or larger than 2 mol %, there is the possibility that the desired absorption properties may not be obtained.

When the monomer component is used in the form of its aqueous solution in the case where reversed-phase suspension polymerization or aqueous solution polymerization is carried out in the polymerization step, the concentration of the monomer component in this aqueous solution (hereinafter referred to as "aqueous monomer solution") is in the range of preferably 10 to 70 wt %, more preferably 15 to 65 wt %, still more preferably 30 to 55 wt %, in terms of the resulting properties, although not especially limited. In addition, when the above aqueous solution polymerization or reversed-phase suspension polymerization is carried out, a solvent other than water may be used therewith in combination if necessary, and the kind of this solvent as used in combination is not especially limited.

In carrying out the polymerization, a water-soluble resin or a water-absorbent resin of 0 to 50 t %, for example, preferably 0 to 20 wt %, as various foaming agents (e.g. carbonate, azo compounds, bubbles), surfactants, chelating agents, and chain transfer agents in amounts of 0 to 5 wt %, for example, preferably 0 to 1 wt % can be added for improving the properties of the water-absorbent resin.

(7) Step of Carrying Out Polymerization (Step (a))

In the step of polymerizing the monomer component, from the viewpoint of the performance or the ease of controlling the polymerization, aqueous solution polymerization or reversed-phase suspension polymerization is carried out in such a manner that the above monomer component is used in the form of its aqueous solution. These polymerization methods can be carried out in an air atmosphere. The polymerization methods are preferably carried out in an atmosphere of an inert gas such as nitrogen or argon (e.g. 1% oxygen or oxygen lower than 1%). In addition, the monomer component is used for polymerization preferably after oxygen dissolved therein has sufficiently been displaced with the inert gas (e.g. oxygen lower than 1 ppm). The present invention is particularly preferable for the aqueous solution polymerization which is of high productivity and gives high properties but conventionally involves difficulty in controlling the polymerization. Examples of particularly preferable aqueous solution polymerization include continuous belt polymerization and continuous or batch kneader polymerization.

The reversed-phase suspension polymerization is a polymerization method in which the aqueous monomer solution is suspended into a hydrophobic organic solvent, and examples thereof are disclosed in U.S. patents such as U.S. Pat. No. 4,093,776, U.S. Pat. No. 4,367,323, U.S. Pat. No. 4,446,261, U.S. Pat. No. 4,683,274, and U.S. Pat. No. 5,244,735. The aqueous solution polymerization is a polymerization method in which the aqueous monomer solution is polymerized without using any dispersion solvent, and examples thereof are disclosed in U.S. patents such as U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, and U.S. Pat. No. 5,380,808, and in European patents such as EP 0811636, EP 0955086, EP 0922717, and EP 1178059. Monomers, cross-linking agents, polymerization initiators, and other additives which are described in the patent documents listed above are applicable to the present invention.

Furthermore, in the present invention, on the occasion when the aforementioned monomer component is polymerized, the total time between the end of the preparation of the monomer component and/or neutralization of the acrylic acid and the initiation of the polymerization is preferably as short as possible in order to attain (i) the improved absorption properties and (ii) the less colored water-absorbent resin, both of which are the goals of the present invention. Specifically, the polymerization is initiated preferably within 24 hours, more preferably within 12 hours, still more preferably within 3 hours, particularly preferably within 1 hour, after the preparation of the monomer component and/or neutralization of the acrylic acid. Industrially, the neutralization and/or the preparation of the monomer component are carried out in large quantities in tanks. Therefore it is usual that the residence time exceeds 24 hours. However, it has been discovered by the present inventors that the longer time it is after the preparation of the monomer component and/or neutralization of the acrylic acid, the more the residual monomer content and the coloration are deteriorated. Thus, to shorten the residence time, the neutralization and the preparation of the monomer component are continuously made to carry out the polymerization batchwise or continuously. Preferably, the polymerization is carried out continuously.

On the occasion when the above aqueous monomer solution is polymerized, at least one of the following polymerization initiators, for example, can be used: persulfate salts such as potassium persulfate, ammonium persulfate, and sodium persulfate; and t-butyl hydroperoxide, hydrogen peroxide, 2,2'-azobis(2-amidinopropane) dihydrochloride, 2-hydroxy-1-phenylpropan-1-one, and benzoin methyl ether. Furthermore, a redox initiator is also available by using the above polymerization initiator jointly with a reducing agent which promotes decomposition of the above polymerization initiator and thus combining both with each other. Examples of the above reducing agent include: sulfurous acid (or (bi) sulfite) such as sodium sulfite and sodium hydrogensulfite; L-ascorbic acid (or its salts); reducible metals (or their salts) such as ferrous salts; and amines; and preferably used is a redox polymerization initiator combining the reducing agent with the persulfate salt and/or the peroxide, but there is no particular limitation thereto. The amount of the above polymerization initiator or reducing agent as used is usually in the range of preferably 0.001 to 2 mol %, more preferably 0.01 to 0.5 mol %, relative to the monomer component.

Of these polymerization initiators, preferably for attaining still lower colorability and lower yellowing of the water-absorbent resin of the present invention, the hydrogen peroxide and/or the (hydrogen)sulfite, more preferably the hydrogen peroxide, are used. Other polymerization initiators, particularly the persulfate or the azo compounds, may further be used in combination with the hydrogen peroxide and/or (hydrogen)sulfite. The quantity of the hydrogen peroxide and/or the (hydrogen)sulfite as used is preferably in the range of 0.00001 to 0.1 g/(mol of monomers), more preferably 0.0001 to 0.01 g/(mol of monomers), and further is smaller than that of the above other polymerization initiators as used jointly therewith. Incidentally, the azo compounds display a good effect on a low coloring, but excessive use of the persulfate results in property deterioration and/or coloration. Therefore the persulfate are used in combination preferably in the aforementioned range.

In addition, the polymerization reaction may be carried out either by irradiating the reaction system with active energy rays, such as radiations, electron beams, and ultraviolet rays, instead of using the above polymerization initiator, or by a combined use of these active energy rays with the above polymerization initiator.

The reaction temperature and time in the above polymerization reaction is not particularly limited and may appropriately be set according to factors such as the respective kinds of the hydrophilic monomer and polymerization initiator and the reaction temperature. However, the polymerization is usually carried out at not higher than the boiling point preferably within 3 hours, more preferably within 1 hour, still more preferably within 0.5 hour, and at a peak temperature of preferably not higher than 150° C., more preferably in the range of 90 to 120° C. In addition, it is also preferable that water and/or acrylic acid as vaporized during the polymerization is, if necessary, collected and then recycled to the process for producing the water-absorbent resin.

In addition, the present invention is fit for production, particularly, continuous production, on a large scale of not smaller than a certain quantity per line. There is a possibility that the effects of the present invention may not sufficiently be displayed in production on a laboratory level or in production at pilot or small-scale plants. However, as to production on a large scale, particularly, of preferably not smaller than 300 Kg/hour, more preferably not smaller than 500 Kg/hour, still more preferably not smaller than 700 Kg/hour, in terms of production per line, it has been discovered by the present inventors that, also from the viewpoint of such as monomer stability and polymerization rate, unless the present invention is applied thereto, the desired water-absorbent resin having sufficient properties is not obtained.

(8) Neutralization after Polymerization

In a first production process of the present invention, generally, a neutralized acid-group-containing unsaturated monomer is polymerized (post-neutralization polymerization). A second production process of the present invention adopts a polymerization method such that acid groups of an unneutralized acid-group-containing unsaturated monomer containing particularly an unneutralized acrylic acid as a main component, are neutralized after polymerization (pre-neutralization polymerization) (For example, U.S. Pat. Nos. 6,187,872, 6,060,557, 5,145,906, 543,323, 6,602,950, and 4,985,514, and Patent document 1).

In the second production process, a crosslinked polymer based on a monomer having an unneutralized acrylic acid content of particularly 30 to 100 mol %, further 90 to 100 mol %, particularly 100 mol. % can be also used in producing a water-absorbent resin of the present invention, in such a manner that the crosslinked polymer is caused to have partially alkali metal bases by addition of the foregoing basic composition, particularly a basic composition containing an alkali metal compound as a basic compound. The water-absorbent resin obtained by the polymerization method in the present invention further improves the relationship between absorption capacity and water-soluble polymer. Thus, it is possible to obtain an absorbent structure having a high absorptive power and an excellent stability for urine. In addition, the use of the foregoing basic composition realizes a less-colored and less-degraded water-absorbent resin.

In the second production process, a hydrogel crosslinked polymer after polymerization is essentially neutralized. In terms of the resultant water-absorbent resin's performance, industrially easy availability, and safety, sodium salt and potassium salt are preferable. In the present invention, 50 to 90 mol %, preferably 60 to 80 mol % of acid groups in the polymer is converted into alkali metal salt by neutralization reaction with alkali metal compound. The neutralization of a hydrogel crosslinked polymer with an alkali metal compound can be realized in such a manner that the hydrogel crosslinked polymer obtained by the polymerization of a solvent is added to an aqueous solution of the alkali metal compound while the hydrogel crosslinked polymer is cut into small pieces of about 1 $cm^3$ or smaller, and the resultant gel is mulled by a kneader or a meat chopper. In order to obtain a water-absorbing agent of the present invention, a neutralization temperature is preferably in the range of 50 to 100° C., more preferably 60 to 90° C. Preferably, the neutralization is carried out so uniformly that a first neutralization coefficient (neutralization degree in 200 polymer particles) recited in claim 1 of U.S. Pat. No. 6,187,872 is not more than 10.

(9) Drying Step (Step (b))

If necessary, the hydrogel crosslinked polymer (hereinafter, also referred to as "hydrogel crosslinked polymer") having been obtained in the polymerization step is disintegrated into small pieces with a gel pulverizer or the like as needed. The disintegrated resultant is dried under a particular temperature condition. Thereafter, if necessary, the dried resultant is pulverized or classified, and further granulated and crosslinked under a particular temperature condition. The water-absorbent resin according to the present invention has excellent properties. Undergoing the foregoing steps realizes the water-absorbent resin having further improved properties and reduced odors.

In addition, in order to attain the objects of the present invention, i.e. the reduction of a residual monomer content and a less colored water-absorbent resin, the time from the end of the polymerization, through a gel-pulverizing step if necessary, until the start of the drying is preferably as short as possible. Specifically, the hydrogel crosslinked polymer starts to be dried (is placed into a dryer) preferably within 1 hour, more preferably within 0.5 hour, still more preferably within 0.1 hour, after the polymerization is completed. In addition, in order to attain the reduction of a residual monomer content and a less colored water-absorbent resin, the temperature of the hydrogel crosslinked polymer is controlled to be preferably in the range of 50 to 80° C., more preferably 60 to 70° C., for the duration between the end of the polymerization and the start of the drying. On industrial occasions, the polymerization is carried out in large quantities, therefore it is also usual that the residence time, after the polymerization, exceeds 3 hours. However, it has been discovered by the present inventors that as the time increases before the start of the drying and/or as the temperature deviates from the above range, the residual monomer content increases or a resultant water-absorbent resin becomes remarkably colored. Thus, preferably, continuous polymerization and continuous drying are carried out to shorten the residence time.

In the present invention, the drying is primarily the operation for removing water, and also for removing an unpolymerizable organic compound having the solubility parameter defined previously.

The solid content of the resin as determined from its weight loss caused by drying (by heating 1 g of powder or particles at 180° C. for 3 hours) is adjusted to be preferably not less than 80 wt %, more preferably in the range of 85 to 99 wt %, still more preferably 90 to 98 wt %, particularly preferably 92 to 97 wt %. In addition, a drying temperature is not particularly limited, but is preferably such that heating in the step (b) is carried out at a temperature not lower than the boiling temperature of the unpolymerizable organic compound. Specifically, the drying temperature is preferably in the range of 100 to 300° C., more preferably 150 to 250° C.

Examples of usable drying methods include various methods such as: heat-drying; hot-air drying; vacuum drying; infrared drying; microwave drying; drum drier drying; dehydration by azeotropy with hydrophobic organic solvents; and high-moisture drying by high-temperature steaming. The preferred drying method is the hot-air drying with a gas having a dew point of preferably 40 to 100° C., more preferably 50 to 100° C., still more preferably 60 to 90° C., in terms of properties of the water-absorbent resin and efficiency in removal of the unpolymerizable organic compound.

(10) Surface-Crosslinking Step (c)

Next, a further explanation is made about the surface-crosslinking in the present invention. The "surface-crosslinking" of the water-absorbent resin means further forming a portion having high crosslinking density in surface layers (neighborhoods of surfaces: neighborhoods usually within several tens of μm from the surfaces) of the water-absorbent resin having a uniformly crosslinked structure inside the polymer. The water-absorbent resin obtained in the present invention has a low water-soluble component content and a high absorption capacity, thus attaining excellent surface-crosslinking effects thereon, exerting more excellent properties and performances, increasing its absorption capacity under pressure (AAP) and liquid permeability under pressure (PPUP), and reducing its odor.

Various surface-crosslinking agents are usable for carrying out the foregoing surface-crosslinking. However, in terms of the properties, crosslinking agents that can react with a carboxyl group are generally used. Examples of such crosslinking agents are: polyhydric alcohol compounds; epoxy compounds; polyamine compounds or condensation products of polyamine compounds and haloepoxy compounds; oxazoline compounds; mono-, di-, or polyoxazolidinone compounds; polyvalent metal salts; and alkylene carbonate compounds.

The surface-crosslinking agent as used in the present invention is specifically exemplified in such as U.S. Pat. No. 6,228,930, U.S. Pat. No. 6,071,976, and U.S. Pat. No. 6,254,990. Examples thereof include: polyhydric alcohol compounds such as mono-, di-, tri-, tetra-, or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol; epoxy compounds such as ethylene glycol diglycidyl ether and glycidol; polyamine compounds such as ethylenediamine, diethylenetriamine, triethylenetetramine, tetraethylenepentamine, pentaethylenehexamine, polyethylenimine, and polyamidopolyamines; haloepoxy compounds such as epichlorohydrin, epibromohydrin and α-methylepichlorohydrin; condensation products between the above polyamine compounds and the above haloepoxy compounds; oxazolidinone compounds such as 2-oxazolidinone; and alkylene carbonate compounds such as ethylene carbonate. However, there is no particular limitation. Of these crosslinking agents, at least the polyhydric alcohols are used preferably for maximizing the effects of the present invention, and polyhydric alcohols having 2 to 10 carbon atoms, preferably 3 to 8 carbon atoms, are used.

The quantity of the surface-crosslinking agent as used depends upon factors such as the types of the compounds used and combinations thereof, but is preferably in the range of 0.001 to 10 parts by weight, more preferably 0.01 to 5 parts by weight, relative to 100 parts by weight of the solid content of the resin. In the present invention, water is preferably used for the surface-crosslinking. The quantity of water, as used on this occasion, depends upon the water content of the water-absorbent resin as used, but is usually in the range of preferably 0.5 to 20 parts by weight, more preferably 0.5 to 10 parts by weight, relative to 100 parts by weight of the water-absorbent resin. In addition, in the present invention, a hydrophilic organic solvent may be used as an alternative to water. The quantity of the hydrophilic organic solvent, as used on this occasion, is usually in the range of preferably 0 to 10 parts by weight, more preferably 0 to 5 parts by weight, still more preferably 0 to 3 parts' by weight, relative to 100 parts by weight of the water-absorbent resin. The temperature of the crosslinking agent solution is preferably set in the range of 0° C. to boiling point, more preferably 5 to 50° C., still more preferably 10 to 30° C., in terms of the mixability and stability. In addition, before mixing with cross-linking agent solution, the temperature of the water-absorbent resin powder is preferably in the range of 0 to 80° C., more preferably 40 to 70° C., in terms of the mixability.

Furthermore; in the present invention, one preferred mixing method is a method including the steps of premixing the surface-crosslinking agent with water and/or the hydrophilic organic solvent, if necessary, and then spraying or dropwise adding (preferably, spraying) the resultant aqueous solution to the water-absorbent resin to mix them together. The size of the liquid droplets as sprayed averages preferably 1 to 300 µm, more preferably 10 to 200 µm. In addition, in the mixing step, there may be allowed to coexist water-insoluble fine-particulate powder and/or surfactants within the range not damaging the effects of the present invention, for example, within the range of 0 to 10 wt %, preferably 0 to 5 wt %, more preferably 0 to 1 wt %, relative to the water-absorbent resin. The surfactants as used and their quantities are exemplified in the International publication WO2005JP1689 (International filing date: Feb. 4, 2005).

A preferable mixing apparatus as used for the aforementioned mixing step needs to be able to generate great mixing power to ensure homogeneous mixing. Various mixing machines are usable in the present invention, but preferably they are high-speed agitation type mixers, particularly preferably, high-speed agitation type continuous mixers. Examples of such mixers are Turbulizer (product name; produced by Hosokawa Milkron Co., Ltd. of Japan) and Lödige Mixer (product name; produced by Gebruder Lödige Maschinenbau GmbH of Germany).

After mixing with the surface-crosslinking agent, the resulting water-absorbent resin preferably is subjected to the heating treatment. The above heating treatment is preferably carried out under the conditions where the heating temperature in the step (c) is not lower than a boiling temperature of the unpolymerizable organic compound. The heating temperature is preferably in the range of 120 to 250° C., more preferably 150 to 250° C. The heating time is preferably in the range of 1 minute to 2 hours. The heating treatment can be carried out by using conventional dryers or heating-furnaces. Examples of the dryers include channel type blending dryers, rotary dryers, disk dryers, fluidized-bed dryers, gas blowing type (pneumatic type) dryers, and infrared dryers. In addition, after being heated, the water-absorbent resin may be cooled, if necessary.

These surface-crosslinking methods are also disclosed in: various European patents such as European Patent Nos. 0349240, 0605150, 0450923, 0812873, 0450924, and 0668080; various Japanese patents such as Japanese Unexamined Patent Publication Nos. 242709/1995 and 224304/1995; various U.S. patents such as U.S. Pat. Nos. 5,409,771, 5,597,873, 5,385,983, 5,610,220, 5,633,316, 5,674,633, and 5462972; and various international patent publications such as WO 99/42494, WO 99/43720, and WO 99/42496. These surface-crosslinking methods are also applicable to the present invention.

(11) Properties and Shape of the Water-Absorbent Resin

The shape of the water-absorbent resin as obtained in the present invention is not especially limited, but examples thereof include: particulate or powder form such as irregular pulverized form and spherical form; and gel form, sheet form, rodlike form, fibrous form, and film form. In addition, the resin may be combined with or supported on materials such as fibrous materials. However, generally, the water-absorbent resin is preferably in particulate or powder form, considering the uses for the water-absorbent resin, such as absorbent articles and gardening and tree planting. In the case where the water-absorbent resin is in powder form, it may be granulated particles or primary particles, and the weight-average particle diameter thereof before or after the surface cross-linking is usually in the range of 10 to 2000 µm. In the present invention, the granulated particles are also referred to as agglomerate particles. In terms of the properties, the weight-average particle diameter is preferably in the range of 100 to 1000 µm, more preferably 200 to 600 µm, particularly preferably 300 to 500 µm. The quantity of particles having particle diameters in the range of 850 to 150 µm is in the range of 90 to 100 wt %, in the range of 95 to 100 wt %, particularly in the range of 98 to 100 wt %.

The water-absorbent resin of the present invention improves the relationship between absorption capacity and water-soluble polymer which are conflicting properties of a water-absorbent resin. Thus, the water-absorbent resin of the present invention can have still higher properties by being subjected to surface-crosslinking.

More specifically, the water-absorbent resin according to the present invention preferably has a absorption capacity of not less than 15 g/g, more preferably not less than 20 g/g, still more preferably not less than 23 g/g, yet more preferably 25 g/g for a physiological saline solution under pressure (4.9 kPa). In addition, the absorption capacity for a physiological saline solution under pressure (1.9 kPa) is also usually not less than 15 g/g, preferably not less than 20 g/g, more preferably not less than 25 g/g, still more preferably 28 g/g, particularly preferably not less than 32 g/g. The absorption capacity without pressure (GVs) is also not less than 25 g/g, more preferably not less than 28 g/g, particularly preferably not less than 32 g/g. There are no particular upper limits for the absorption capacity under pressure and the absorption capacity without pressure. However, the upper limits therefor are usually in the order of 60 g/g, in terms of (i) balance with other properties and (ii) costs.

Furthermore, liquid-permeability under pressure (PPUP) is preferably in the range of 20 to 100%, more preferably 30 to 100%, still more preferably 40 to 100%, most preferably 50 to 100%.

Note that, the liquid permeability under pressure, which is different from the absorption capacity under pressure (AAP: 0.9 g), is a measure of the stability of the absorption capacity under pressure (AAP) (freedom from reduction in absorption capacity under pressure) when the amount of water-absorbent resin (the amount of resin per unit area in measurement) is increased from 0.90 g to 5.0 g. The liquid permeability under pressure is a new parameter defined in the present invention. For example, the amount of water-absorbent resin (the amount of resin per unit area in measurement) can vary by site even in the same diaper. Varied absorption capacity under pressure (AAP), which is caused by the amount of water-absorbent resin varying by site in the diaper, is the cause of degraded properties of the diaper in actual use. When the liquid permeability under pressure (PPUP) defined in Example as will be hereinafter described is very high, the diaper can stably exhibit high properties, regardless of the amount (concentration) of water-absorbent resin in the diaper, and can also exhibit a high liquid permeability. Details of the liquid permeability under pressure (PPUP) is described in Japanese Patent Application No. 109779/2005 (filed on Apr. 6, 2005) and the descriptions of Japanese Patent Application No. 109779/2005 are also applied to the present invention.

The water-soluble component content of the water-absorbent resin obtained in the production process of the present invention is preferably not more than 25 wt %, more preferably not more than 15 wt %, still more preferably 10 wt %.

Further, a GEX value (defined in Example) defined according to the relationship between absorption capacity (GVs) and an soluble content is preferably not less than 17, more preferably not less than 18, particularly preferably not less than 19.

In addition, as is specified in the below-mentioned description of examples of some preferred embodiments of the present invention and in the aforementioned object of the present invention, the water-absorbent resin according to the present invention is less colored (little or no yellow coloration), and has a low residual monomer content. Specifically, its colored state indicates a YI value (Yellow Index, see European Patent Nos. 0942014 and 1108745) preferably in the range of 0 to 15, more preferably 0 to 13, still more preferably 0 to 10, most preferably 0 to 5, so there is almost no tinge of yellow. Furthermore, the residual monomer content is low and preferably in the range of 0 to 400 ppm by weight, more preferably 0 to 300 ppm by weight.

In order to cause the water-absorbent resin of the present invention to have various functions, materials such as chelating agents, oxidizers, reducing agents such as (hydrogen) sulfite, chelating agents such as amino carboxylic acid, water-insoluble inorganic powder or water-insoluble organic powder, deodorizers, antimicrobial agents, and polymer polyamine, in a quantity of 0 to 10 parts by weight, preferably 0 to 1 parts by weight.

(12) Addition of Chelating Agent

For the promotion of polymerization, the prevention of coloration, and the prevention of deterioration, the present invention can preferably add a chelating agent, particularly a polyvalent carboxylic acid and its salt of more than 0 ppm, preferably 10 ppm to 1%, to (a) a monomer before being polymerized or (b) a hydrogel crosslinked polymer after been polymerized, prior or subsequent to the neutralization of the (a) or (b). The chelating agent is preferably added in an aqueous solution form (0.1 to 10% water relative to a water-absorbent resin).

A chelating agent suitable for use in a particulate water-absorbing agent of the present invention is preferably a chelating agent having high ion blocking or chelating ability to Fe or Cu. More specifically, the chelating agent is: preferably a chelating agent having a stability constant to Fe ion of at least 10, preferably at least 20; more preferably amino polycarboxylic acid and its salt, particularly preferably amino polycarboxylic acid having at least three carboxyl groups and its salt.

Examples of amino polycarboxylic acid include diethylenetriaminepentaacetate, triethylenetetraaminehexaacetate, cyclohexane-1,2-diaminetetraacetate, N-hydroxyethylethylenediaminetriacetate, ethylene glycol diethyl ether diaminetetraacetate, ethylenediaminetetrapropionate, N-alkyl-N'-carboxymethyl aspartate, N-alkenyl-N'-carboxymethyl aspartate, and their alkaline metal salts, alkaline earth metal salts, ammonium salts, and amine salts. Among these, diethylenetriaminepentaacetate, triethylenetetraaminehexaacetate, N-hydroxyethylethylenediaminetriacetate, and their salts are most preferable.

(13) Uses of the Water-Absorbent Resin According to the Present Invention

The process according to the present invention provides the easy production of a water-absorbent resin having good absorption properties in excellent balance between the absorption capacity without pressure (=GVs=Gel Volume in saline=Centrifuge retention capacity), the absorption capacity under pressure (AAP), and the soluble content. The resulting water-absorbent resin is widely used for various purposes such as agricultural and horticultural water-retaining agents, industrial water-retaining agents, humidity-absorbing agents, dehumidifying agents, and building materials, but the water-absorbent resin according to the present invention is particularly preferably used for sanitary materials such as disposable diapers, incontinent pads, mother's breast pads (nursing pads), and sanitary napkins.

Furthermore, the water-absorbent resin according to the present invention is so excellent with regard to the above properties being in good balance that the water-absorbent resin can be used in the sanitary materials (e.g. disposable diapers) in high concentrations where the water-absorbent resin concentration (weight ratio of the water-absorbent resin to the total weight of the water-absorbent resin and fibrous materials), is preferably 30 to 100 wt %, more preferably 40 to 100 wt %, still more preferably 50 to 95 wt %.

EXAMPLES

Hereinafter, the present invention will be described according to Examples below. However, the present invention is not limited to the descriptions of Example. In addition, the properties, as recited in the claims of the present invention and in Examples of the present invention, were determined by the following measurement methods.

(1) Absorption Capacity without Pressure (=GVs=Gel Volume in Saline=Centrifuge Retention Capacity)

0.2 g of water-absorbent resin was uniformly placed into a bag (60 mm×60 mm) made of nonwoven fabric. The bag was sealed and then immersed into 100 g of a 0.9 wt % aqueous sodium chloride solution (physiological saline solution) of which the temperature had been adjusted to 25 (±3)° C. After 60 minutes, the bag was pulled up and then drained of water by a centrifugal force of 250 G with a centrifugal separator for 3 minutes, and then the weight W1 of the bag was measured. In addition, the same procedure as the above was carried out without the water-absorbent resin, and the resultant weight W2 was measured. Then, the absorption capacity was calculated from these W1 and W2 according to the following equation (1):

$$GVs = (W1-W2)/0.2-1 \qquad \text{(Equation 1).}$$

(2) Water-Soluble Polymer Content (which May be Also Referred to as "Soluble Component Content" and "Soluble Content")

Into a plastic receptacle of 250 ml in capacity having a lid, 184.3 g of 0.90 wt % aqueous sodium chloride solution was weighed out. Then, 1.00 g of water-absorbent resin was added to this aqueous solution, and they were stirred for 16 hours, thereby soluble components were extracted from the resin. The resultant extract liquid was filtrated with a filter paper (produced by ADVANTEC Toyo Co., Ltd., trade name: (JIS P 3801, No. 2), thickness: 0.26 mm, diameter of captured particles: 5 μm), and then 50.0 g of the resultant filtrate was weighed out and used as a measuring solution.

To begin with, only the physiological saline solution was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml). The same titration procedure was carried out also for the measuring solution, thus obtaining titration amounts ([NaOH] ml and [HCl] ml). For example, if the water-absorbent resin comprised acrylic acid and its sodium salt in known amounts, the soluble component content (content of an extracted water-soluble polymer as a main component) of the water-absorbent resin was calculated from the average molecular weight of the monomers and the titration amounts, as obtained from the above procedures, in accordance with the following equation (2). In the case of unknown amounts, the average molecular weight of the monomers was calculated from the neutralization ratio as determined by the titration according to the following equation (3).

Soluble component content(wt %)=0.1×(average molecular weight)×184.3×100×([HCl]−[bHCl])/1000/1.0/50.0     (Equation 2).

Neutralization ratio(mol %)=[1−([NaOH]−[bNaOH])/([HCl]−[bHCl])]×100     (Equation 3).

(3) GEX Value

Normally, the higher the absorption capacity (GVs), the higher the water-soluble component content. Thus, important for a water-absorbent resin is the relationship between a GVs value and a water-soluble component content (x), which are conflicting properties of the water-absorbent resin. The GEX value is a measure for evaluating the above relationship in the case when x exceeds 1 weight %. The higher the GEX value, the higher the performance.

When the GVs value and the soluble component content are denoted by y (g/g) and x (weight %), respectively, the GEX value is defined by the following equation 4:

GEX value=(y)/ln(x)     (Equation 4).

Note that, as to the GVs value γ (g/g) and the soluble component content (wt %) required for the calculation of the GEX value, the values obtained in Sections (1) and (2) above are used.

(4) Residual Monomer Content

The residual monomer (residual acrylic acid and its salt) content of the water-absorbent resin powder, after drying, was determined in the following way. In Section (2) above, a filtrate, as separately prepared after stirring for 2 hours, was UV-analyzed by liquid chromatography to also analyze the residual monomer content ppm (relative to water-absorbent resin) of the water-absorbent resin. In addition, the residual monomer content of the hydrogel polymer, before drying, was determined by: stirring a finely disintegrated hydrogel polymer of about 500 mg in solid resin content for 16 hours; and then UV-analyzing its filtrate by liquid chromatography likewise; and then correcting the solid content.

(5) Absorption Capacity Under Pressure (AAP)

(a) Absorption Capacity for 0.9 Wt % Aqueous Sodium Chloride Solution Under Pressure of 4.9 kPa (AAP: 0.90 g/Absorbency Against Pressure)

A stainless metal gauze, which was a screen of 400 meshes (mesh opening size: 38 μm), was fused to a bottom of a plastic supporting cylinder having an inner diameter of 60 mm. Then, onto the above metal gauze, there was uniformly spread 0.900 g of water-absorbent resin (particulate water-absorbing agent), and further thereon, there were mounted a piston (cover plate), wherein the piston had an outer diameter of only a little smaller than 60 mm and made no gap with the inner wall surface of the supporting cylinder, but was not hindered from moving up and down. Then, the weight W3 (g), i.e. total weight of the supporting cylinder, the water-absorbent resin (or particulate water-absorbing agent), and the piston was measured. Onto this piston, a load was placed on the piston, wherein the load was adjusted so that a load of 4.9 kPa including the weight of the piston could uniformly be applied to the water-absorbent resin (or particulate water-absorbing agent). This completed one set of measurement apparatus. A glass filter having a diameter of 90 mm and a thickness of 5 mm was mounted inside a Petri dish having a diameter of 150 mm, and then a physiological saline solution of which the temperature was adjusted to 25±2° C. was added up to the same level as the upside of the glass filter, on which a filter paper (produced by Toyo Roshi Kaisha, Ltd.; No. 2) having a diameter of 9 cm was then mounted so that its entire surface would be wetted, and further, an excess of liquid was removed.

The one set of measurement apparatus was mounted on the above wet filter paper, thereby getting the liquid absorbed under the load. The liquid level was topped off by adding the liquid from the upper side of the glass filter, so that the liquid was kept at a constant liquid level. After 1 hour, the one set of measurement apparatus was lifted to remove the load, and weight W4 (g) (total weight of the supporting cylinder, a swelling water-absorbent resin (or particulate water-absorbing agent), and the piston) was measured. Then, the absorption capacity under pressure (g/g) was calculated from the W3 and W4 in accordance with the following equation:

Absorption Capacity under Pressure(AAP: 0.90 g)(g/g)=(Weight W4(g)−Weight W3(g))/weight(g)of water-absorbent resin(or particulate water-absorbing agent).

(b) Liquid Permeability Under Load (PPUP/Permeability Potential Under Pressure)

In the measurement of the (a) absorption capacity under pressure (AAP: 0.90 g) under 4.9 kPa, the same procedure as above was carried out except that the amount of water-absorbent resin is changed from 0.900 g to 5.000 g, in order to obtain a value of the absorption capacity under pressure (AAP: 5.0 g). In this procedure, a high absorption capacity under pressure (AAP: 5.0 g) can possibly cause an extremely high layer of a swollen water-absorbent resin (or particulate water-absorbing agent). In view of this, the supporting cylinder as used needs to be of a sufficient height. By using the absorption capacities under pressure (AAP: 0.90 g and AAP: 5.0 g) as obtained in the above procedure, a liquid permeability under pressure (PPUP) is obtained by the following equation:

Liquid permeability under pressure(PPUP)(%)=(AAP: 5.0 g(g/g)/AAP:0.90 g(g/g))×100.

The load of 4.9 kPa (0.90 g of water-absorbent resin) is also referred to as AAP 4.9 kPa. If the load is changed to 1.9 kPa, the load 1.9 kPa is referred to as AAP1.9 kPa.

(7) Peak Time and Induction Time:

The temperature of the monomer or of the resultant polymer gel during the polymerization was measured with a thermometer. Assume that the time (minutes) between the addition of an initiator and the rise in temperature of the monomer or of the resultant polymer gel is defined as an induction time, and the time between the addition of an initiator and the reach to the maximum temperature (peak temperature) of the polymerization system is defined as a peak time.

(8) Weight-Average Particle Diameter (D50)

The water-absorbent resin powder or water-absorbing agent was classified by sieving with JIS standard sieves (JIS Z8801-1(2000) or the like sieves) having mesh opening sizes of such as 850 μm, 710 μm, 600 μm, 500 μm, 425 μm, 300 μm, 212 μm, 150 μm, 106 μm, and 75 μm, and then the percentages of the residues on these sieves were plotted on a logarithmic probability paper. Therefrom, the weight-average particle diameter (D50) was read.

The classification was carried out as follows. Under conditions of a room temperature (20 to 25° C.) and a relative humidity of 50±5% RH, 10 g of water-absorbent resin powder or water-absorbing agent was placed onto the JIS standard sieves (THE IIDA TESTING SIEVE: internal diameter=80 mm), and then classified with a sieve shaker (sieve shaker produced by IIDA SEISAKUSHO; Type: ES-65) for 10 minutes. The weight-average particle diameter (D50) is, as described in U.S. Pat. No. 5,051,259 and other publications, a size of a particular mesh opening of a standard sieve capable of causing 50 wt % particles relative to the entire particles to pass through it.

(9) Coloration Evaluation of Water-Absorbent Resin (YI Value)

This was carried out in accordance with European Patent Nos. 942014 and 1108745. Specifically, the coloration evaluation of the water-absorbent resin powder was carried out in the following way using a spectroscopic color difference meter (SZ-Σ80 COLOR MEASURING SYSTEM, produced by Nippon Denshoku Kogyo Co., Ltd.). About 6 g of the water-absorbent resin was filled into the below-mentioned powder-paste sample stand (filling of about 60% of this sample stand) to measure the surface color (YI value (Yellow Index)) of the water-absorbent resin using the above spectroscopic color difference meter under its set conditions (reflection measurement/appendix powder-paste sample stand (inner diameter: 30 mm)/standard round white board No. 2/30 mm Φ projector pipe for powder-paste as the standard) under conditions of a room temperature (20 to 25° C.) and a relative humidity of 50 RH %.

In addition, color difference (L, a, b) or WB (Hunter Color) which is another yardstick is also measurable at the same time by the same method with the same apparatus as the above. The larger L/WB and the smaller a/b indicate that dye coloring is lower and that the color is nearer to being substantially white.

(10) Odor Evaluation

A sample was prepared by the following manner: 2 g of water-absorbent resin particles are sprayed in a polypropylene cup having an internal diameter of 55 mm and a height of 70 mm, and 50 g of ion-exchanged water was poured into the cup so that the water-absorbent resin particles were gelled. After the gelation, the gelled water-absorbent resin particles were sealed hermetically and heated at 30° C. for 1 hour. Thereafter, the odor of the gelled water-absorbent resin particles was evaluated by 10 adult test subjects. As to a polymer gel, the odor of the polymer gel was evaluated with the polymer gel itself directly placed into the polypropylene cup, without being mixed with ion-exchanged water.

The evaluation was determined in the following manner: Evaluation values, which indicate the degree of odor, were given in five levels from "no odor" (0 point) to "strong odor" (5 point). From the evaluation values reported by the 10 adult test subjects, the average evaluation value was determined to obtain an odor point. The odor point low in number indicates less odors.

(11) Measurement of the Amount of Ultraviolet Rays

The amount of ultraviolet rays was measured by using an accumulated UV meter UIT-150 (manufactured by Ushio Inc.) with a receiver UVD-S365 (manufactured by Ushio Inc.) attached thereto. The measurement was carried out under the same conditions, i.e. ultraviolet irradiation location and ultraviolet irradiation time, as those for the polymerization in the production process of a water-absorbent resin.

(12) Quantification of p-methoxyphenol

UV analysis was carried out by liquid chromatography.

(13) Protoanemonin Content and Furfural Content

These were quantitatively analyzed on the basis of standard samples with a gas chromatograph (GC-7A model, produced by Shimadzu Corporation) and a data processor (C-R6A model, produced by Shimadzu Corporation) under the following conditions:

Detector: FID
Quantity of hydrogen: 30 mL/min
Quantity of air: 0.5 L/min
Column: Hard glass tube of 3 mm in inner diameter and 3.1 m in length
Filler: Chromosorb W
Temperature of column incubator: 100° C.
Temperature of sample-injecting part: 150° C.
Flow rate of carrier gas: nitrogen 40 mL/min Production Example 1

Preparation of Acrylic Acid Composition

Commercially available acrylic acid (special-grade reagent available from Wako Pure Chemical Industries, Ltd.), as obtained by catalytic gas phase oxidation, was supplied into the column bottom of a high-boiling-point-impurities-separating column having fifty dual-flow perforated plates, and then distilled in a reflux ratio of 1 and then further re-distilled, thus obtaining an acrylic acid composition (A) (also referred to as purified acrylic acid) comprising acrylic acid at a concentration of not less than 99% and only trace amounts of impurities (mainly, water).

This acrylic acid composition (A) had a p-methoxyphenol content of ND (less than 1 ppm by weight) and also a protoanemonin content of ND (less than 1 ppm by weight) and also a furfural content of ND (less than 1 ppm by weight). In the acrylic acid composition (A), a phenothiazine content was 0 ppm by weight, an aldehyde content was not more than 1 ppm by weight, a maleic acid content was not more than 1 ppm by weight, an acetic acid was 200 ppm by weight, and propionic acid content was 200 ppm by weight.

Acrylic acid composition (A1) was obtained by adding p-methoxyphenol of 80 ppm by weight, protoanemonin of 5 ppm by weight, and furfural of 2 ppm by weight (relative to solid content of acrylic acid) to the acrylic acid composition (A). Similarly, acrylic acid composition (A2) was obtained by adding p-methoxyphenol of 80 ppm by weight, protoanemonin of 14 ppm by weight, and furfural of 2 ppm by weight to the acrylic acid composition (A).

Production Example 2

Preparation of Aqueous Sodium Hydroxide Solution

In a commercially available 48 wt % aqueous sodium hydroxide solution (Kanegafuchi Chemical Ind. Co., Ltd.), a $Fe_2O_3$ content was measured by the ICP light emission analysis, which is described in JISK1200-6. As a result of the measurement, the $Fe_2O_3$ content was 0.5 ppm by weight. From 0.5 ppm by weight, an iron content was calculated. The iron content was 0.35 ppm by weight (0.5×55.85×2÷158.7=0.35). Further, an iron content relative to the solid content of sodium hydroxide was 0.72 ppm by weight (0.35×100÷48=0.72). This aqueous sodium hydroxide solution is referred to as an aqueous sodium hydroxide solution (S1). To the aqueous sodium hydroxide solution (S1), $Fe_2O_3$ was added to obtain aqueous sodium hydroxide solutions (S2), (S3), and (S4) having iron contents of 5 ppm by weight, 8 ppm by weight, and 11 ppm by weight (relative to the solid content of sodium hydroxide), respectively.

Production Example 3

Preparation of Aqueous Sodium Acrylate Solution

A five-necked flask of 5 liters in capacity, as equipped with two dropping funnels, a pH meter, a thermometer, and stirring blades, was charged with 1598 g of ion-exchanged water. In addition, separately, 1280 g of the acrylic acid composition (A1) obtained in Production Example 1 at room temperature and 1488 g of 48 wt % aqueous sodium hydroxide solution (S1) at room temperature described in Production Example 2 were placed into the two dropping funnels respectively, and the 5-litter flask was immersed into a water-cooling bath.

Next, while the temperature of the neutralization reaction system in the 5-litter flask was maintained at not higher than 35° C. Under stirred conditions, the 48 wt % aqueous sodium hydroxide solution (S1) and the acrylic acid composition (A1) were dropwise added into the flask at the same time as each other. The dropwise addition of the acrylic acid composition (A1) was completed in about 35 minutes, and the dropwise addition of the 48 wt % aqueous sodium hydroxide solution (S1) was completed in about 45 minutes. After the completion of the dropwise addition of the acrylic acid composition (A1), its dropping funnel was washed with 100 g of ion-exchanged water, and all the used washing water was then added into the flask. Furthermore, after the completion of the dropwise addition of the 48 wt % aqueous sodium hydroxide solution (S1), its dropping funnel was similarly washed with 100 g of ion-exchanged water, and all the used washing water was then added into the flask. After the completion of all the dropwise additions, the temperature of the resultant solution was adjusted into the range of 20 to 35° C. to age the reaction mixture for 20 minutes. After this aging, an extremely small quantity of the acrylic acid composition (A1) was dropwise added to adjust the pH to 10 (±0.1), thus obtaining an aqueous sodium acrylate solution (SA1) having a concentration of 37 wt % and a neutralization ratio of 100 mol %.

Production Examples 4 through 7

The same procedure as in Production Example 3 was carried out, but the combination of the acrylic acid composition (A1) and the 48 wt % aqueous sodium hydroxide solution (S1) was replaced with the combination of the acrylic acid composition (A1) and the 48 wt % aqueous sodium hydroxide solution (S2), the combination of the acrylic acid composition (A1) and the 48 wt % aqueous sodium hydroxide solution (S3), the combination of the acrylic acid composition (A1) and the 48 wt % aqueous sodium hydroxide solution (S4), the combination of the acrylic acid composition (A2) and the 48 wt % aqueous sodium hydroxide solution (S1). As a result, aqueous sodium acrylate solutions (SA2), (SA3), (SA4), and (SA5) were obtained, each of which has a monomer concentration of 37 wt % and a neutralization ratio of 100 mol %.

[Production of Water-Absorbent Resin]

Example 1

In a kneader equipped with two sigma type blades, prepared was an aqueous acrylic acid (salt) monomer solution having a monomer concentration of 38 wt % and a neutralization ratio of 75 mol %. This aqueous acrylic acid (salt) monomer solution was prepared by mixing together the acrylic acid composition (A1) obtained in Production Example 1 and the aqueous sodium acrylate solution (SA1) obtained in Production Example 3, and ion-exchanged water. Into the aqueous acrylic acid (salt) monomer solution, polyethylene glycol diacrylate (n=9) as an internal-crosslinking agent was dissolved in an amount of 0.05 mol % to the monomer.

Then, nitrogen gas was introduced into the aqueous monomer solution, whereby the aqueous monomer solution was deaerated with nitrogen gas in the entire reaction container, and an oxygen content of the aqueous monomer solution was reduced to less than 1 ppm. Then, while the aqueous monomer solution was similarly stirred with the two sigma type blades going round, there was added a polymerization initiator comprising sodium persulfate in an amount of 0.05 mol % and L-ascorbic acid in an amount of 0.0006 mol %, whereby polymerization was carried out in the kneader. As a result, a hydrogel crosslinked polymer (1) having an average particle diameter of about 2 mm was obtained. Immediately after the polymerization, the obtained hydrogel polymer (1) was dried for 45 minutes in a hot air dryer at 170° C. The resultant dried product was crushed with a roller mill crusher, and dried product particles having passed through JIS standard sieve of 850 μm were then classified, thus obtaining a water-absorbent resin powder (P1) having a weight-average particle diameter of 390 μm wherein the percentage of particles having a particle diameter of not more than 150 μm is 3%.

Example 2

A water-absorbent resin powder (P2) was obtained as in Example 1, but the aqueous sodium acrylate solution SA2 was used instead of the aqueous sodium acrylate solution SA1.

Example 3

A solution (I) was prepared by mixing together 229 g of the acrylic acid composition (A1), 0.75 g of polyethylene glycol diacrylate (n=9), 0.014 g of 45 wt % aqueous trisodium diethylenetriamine pentaacetate solution, and 0.028 g of Irgacure 184 (manufactured by Ciba Specialty Chemicals). An aqueous sodium hydroxide solution (II) was prepared by mixing together 187.6 g of 48 wt % aqueous sodium hydroxide solution (S1) and 200 g of ion-exchanged water. The solution (I), while being stirred, was mixed with the aqueous sodium hydroxide solution (II). As a result, a monomer solution of which liquid temperature had risen to approximately 98° C. by heat of neutralization and heat of dissolution was obtained. Then, 3.86 g of 10 wt % aqueous sodium persulfate solution was added to the obtained monomer solution. The resultant solution, immediately after having been stirred for several seconds, was injected into an aluminum container having a bottom surface of 250 mm×250 mm in an open system. The aluminum container has a Teflon® tape attached inside and placed on a hot plate at 130° C. Polymerization proceeded while water vapors, expansion, and foaming occurred in all directions. After a lapse of 3 minutes from the injection, a hydraged polymer in thin-sheet form was obtained. During the time period between the point when 1.5 minutes had elapsed and the point when 3 minutes had elapsed after the injection, the solution was irradiated with ultraviolet rays at an irradiation intensity of 1.15 mW/cm$^2$ by using a UV lump (TOSCURE401; produced by Toshiba). The resultant polymer, after having been cut finely, was dried for 40 minutes in a hot air drier in which the temperature was set to 180° C. The resultant dried product was crushed with a roller mill crusher, and dried product particles having passed through JIS standard sieve of 850 μm were then classified, thus obtaining a water-absorbent resin powder (P3) having a weight-average particle diameter of 390 μm wherein the percentage of particles having a particle diameter of not more than 150 μm is 3%.

Example 4

A cylindrical polypropylene container of 1 liter in capacity with a lid was prepared as a polymerization container. An aqueous monomer solution (4) having a p-methoxyphenol content of 20 ppm by weight, a monomer concentration of 20 wt % and a neutralization ratio of 0 mol % was obtained by mixing together 72.07 g of the acrylic acid composition (A1) obtained in Production Example 1, 293.06 g of ion-exchanged water, and polyethylene glycol diacrylate (molar-number-average degree "n" of addition polymerization of ethylene oxide=8.2) as an internal-crosslinking agent in an amount of 0.05 mol % (to the entire monomers). Furthermore, while being kept at 20° C., this aqueous monomer solution (4) was charged into the above cylindrical container, and then nitrogen gas was introduced into the solution to deaerate the solution with nitrogen gas to reduce its dissolved oxygen content to not more than 1 ppm. Next, while the cylindrical container was thermally insulated in an adiabatic state, a polymerization initiator, comprising a combination of an aqueous sodium persulfate solution (of the ratio of 0.12 g/(mol of entire monomers) (hereinafter abbreviated to g/mol)) with an aqueous solution of L-ascorbic acid (of the ratio of 0.0018 g/mol), was added to the aqueous monomer solution (4) to initiate static polymerization. After a certain time, the polymerization started and then was allowed to proceed and then, after having reached the peak temperature, the polymerization was continued for another 30 minutes, thus obtaining a cylindrical hydrogel crosslinked polymer (4). The resultant hydrogel crosslinked polymer (4) was finely disintegrated into pieces of the size of about 1 mm, and then thereto 62.5 g of 48 wt % aqueous sodium hydroxide solution (S1) was added to neutralize 75 mol % of acid groups of the polymer.

With regard to the neutralized hydrogel crosslinked polymer (4) as obtained in the above manner, the polymerization conversion was 98.4% (the residual monomer content was 16000 ppm by weight). Next, the above hydrogel was spread onto a metal gauze of 850 μm, and then hot-wind-dried with a gas of 160° C. (dew point: 60° C.) for 60 minutes, and then pulverized with a vibration mill, and dried product particles having passed through JIS standard sieve of 850 μm were then classified, thus obtaining a water-absorbent resin powder (P4) having a weight-average particle diameter of 380 μm wherein the percentage of particles having a particle diameter of not more than 150 μm is 2%.

Example 5

100 parts by weight of the water-absorbent resin powder (P4) was spraywise mixed with a surface-crosslinking agent comprising 0.4 parts by weight of 1,4-butanediol, 0.6 parts by weight of propylene glycol, 3.0 parts by weight of ion-exchanged water, and 0.5 parts by weight of isopropanol, 0.01 parts by weight of diethylenetriamine pentaacetate, and the resultant mixture was heat-treated at 210° C. for 40 minutes, thus obtaining a surface-crosslinked water-absorbent resin powder (P5). The water-absorbent resin powder (P5) had the following properties: AAP1.9 kPa=28 g/g; AAP4.9 kPa=25 g/g; and PPUP=50%.

Example 6

A water-absorbent resin powder (P10) was obtained as in Example 5, but the water-absorbent resin powder (P1) was used instead of the water-absorbent resin powder (P4). The water-absorbent resin powder (P10) had the following properties: AAP1.9 kPa=30 g/g; AAP4.9 kPa=28 g/g; and PPUP=60%.

Example 7

A water-absorbent resin powder (P11) was obtained as in Example 5, but the water-absorbent resin (P2) was used instead of the water-absorbent resin powder (P4). The water-absorbent resin powder (P11) had the following properties: AAP1.9 kPa=29 g/g; AAP4.9 kPa=24 g/g; and PPUP=58%.

Comparative Example 1

A water-absorbent resin powder (P6) was obtained as in Example 1, but the aqueous sodium acrylate solution (SA3) was used instead of the aqueous sodium acrylate solution (SA1).

Comparative Example 2

A water-absorbent resin powder (P7) was obtained as in Example 1, but the aqueous sodium acrylate solution (SA4) was used instead of the aqueous sodium acrylate solution (SA1).

Comparative Example 3

A water-absorbent resin powder (P8) was obtained as in Example 1, but the acrylic acid composition (A2) was used instead of the acrylic acid composition (A1), and the aqueous sodium acrylate solution (SA2) was used instead of the aqueous sodium acrylate solution (SA1).

Comparative Example 4

A water-absorbent resin powder (P9) was obtained as in Example 3, but the aqueous sodium acrylate solution (S4) was used instead of the 48 wt % aqueous sodium acrylate solution (S1).

Comparative Example 5

A water-absorbent resin powder (P12) was obtained as in Example 5, but the water-absorbent resin (P9) was used instead of the water-absorbent resin powder (P4). The water-absorbent resin powder (P12) had the following properties: AAP1.9 kPa=15 g/g; AAP4.9 kPa=12 g/g; and PPUP=11%.

(Analysis Results of Water-Absorbent Resins) Table 1

Table 1 shows polymerization time, water-soluble component content, and color phase of the water-absorbent resins obtained in Examples 1 through 4 and Comparative Examples 1 through 4.

As described in Patent document 3, it has been known that a heavy metal content of more than 0.1 ppm by weight in an aqueous monomer solution increases a residual monomer content in a water-absorbent resin. On the contrary, as is apparent from comparisons between Examples 1 and 2 and Comparative Examples 1 through 4 all of which adopted the same polymerization method, the process of the present invention including the step of preparing a monomer by using (i) acrylic acid containing particular trace components and (ii) a basic composition containing iron ($Fe_2O_3$) in particular amounts (0.2 to 5 ppm by weight) and a basic compound (caustic soda), realizes the shortening of the polymerization time, reduction in water-soluble component content, the improvement of the GEX value, and a less-colored water-absorbent resin having no odor.

Different from the water-absorbent resins obtained in Comparative Examples 1 and 2, the water-absorbent resins obtained in Examples 1 and 2 showed no deterioration of the gel (urine deterioration) even after the water-absorbent resins were was swollen at an absorption capacity of 25 times at 37° C. and left standing for 16 hours, although not shown in Table 1.

TABLE 1

| | Example 1 | Example 2 | Example 3 | Example 4 | Comparative Example 1 | Comparative Example 2 | Comparative Example 3 | Comparative Example 4 |
|---|---|---|---|---|---|---|---|---|
| acrylic acid composition | A1 | A1 | A1 | A1 | A1 | A1 | A2 | A1 |
| protoanemonin (ppm) | 5 | 5 | 5 | 5 | 5 | 5 | 14 | 5 |
| furfural (ppm) | 2 | 2 | 2 | 2 | 2 | 2 | 2 | 2 |
| methoxyphenol (ppm) | 80 | 80 | 80 | 80 | 80 | 80 | 80 | 80 |
| aqueous sodium hydroxide solution | S1 | S2 | S1 | S1 | S3 | S4 | S1 | S4 |
| iron (ppm) | 0.7 | 5 | 0.7 | 0.7 | 8 | 11 | 0.7 | 11 |
| polymerization time (min) | 10.8 | 12.8 | 3.0 | 10.8 | 13.8 | 14.2 | 16.3 | 3.0 |
| water-absorbent resin powder | P1 | P2 | P3 | P4 | P6 | P7 | P8 | P9 |
| water-absorption capacity (g/g) | 37.2 | 37.7 | 42.0 | 37.2 | 38.4 | 38.9 | 42.0 | 52.0 |
| water-soluble component content (weight %) | 7.6 | 7.7 | 14.0 | 7.6 | 9.4 | 10.0 | 10.0 | 33.5 |
| GEX value | 18.3 | 18.5 | 22.3 | 18.3 | 17.1 | 16.9 | 18.2 | 19.5 |
| color phase WB | 69.9 | 70.2 | 70.9 | 69.9 | 66.2 | 65.4 | 69.4 | 64.9 |
| L | 87.4 | 87.5 | 89.85 | 87.4 | 85.9 | 85.5 | 87.2 | 85.25 |
| a | −0.7 | −0.6 | −0.8 | −0.7 | −0.1 | 0.1 | −0.6 | 0.0 |
| b | 5.3 | 5.2 | 5.66 | 5.3 | 6.2 | 6.5 | 5.3 | 6.78 |
| coloration (by visual observation) | white | white | white | white | yellow | yellow | white | yellow |

INDUSTRIAL APPLICABILITY

The present invention makes it possible to produce, with a high productivity, a water-absorbent resin having an improved relationship between absorption capacity and water-soluble polymer, which are conflicting properties of the water-absorbent resin, being easily controlled for polymerization reaction, being of no odor, being less colored, and being of high absorption properties.

The invention claimed is:

1. A process for producing a polyacrylic acid (salt) water-absorbent resin by polymerizing an acrylic acid composition including acrylic acid and/or its salt as a main component, the process comprising (a) a step of neutralizing the acrylic acid included in the acrylic acid composition with a basic composition; and
then polymerizing a resultant product, thereby forming a hydrogel crosslinked polymer,
wherein the acrylic acid included in the acrylic acid composition comprises:
 (i) a methoxyphenol content of 10 to 200 ppm by weight relative to the weight of the acrylic acid;
 (ii) at least one compound content of which is 0 to 10 ppm by weight relative to the weight of the acrylic acid, the compound being selected from the group consisting of protoanemonin and furfural; and
 (iii) β-hydroxypropionic acid and/or acrylic acid dimer in an amount of 1 to 1000 ppm by weight relative to the weight of the acrylic acid;
the basic composition including a basic compound and iron,
the basic composition having an iron content of 0.14 to 3.5 ppm by weight, and
the water-absorbent resin having a liquid permeability under pressure (PPUP) in a range of 50 to 100%.

2. A process for producing a polyacrylic acid (salt) water-absorbent resin by polymerizing an acrylic acid composition including acrylic acid and/or its salt as a main component,
the process comprising (a') the step of polymerizing the acrylic acid included in the acrylic acid composition to thereby form a hydrogel crosslinked polymer; and neutralizing the hydrogel crosslinked polymer with a basic composition,
wherein the acrylic acid included in the acrylic acid composition comprises:
 (i) a methoxyphenol content of 10 to 200 ppm by weight relative to the weight of the acrylic acid;
 (ii) at least one compound content of which is 0 to 10 ppm by weight relative to the weight of the acrylic acid, the compound being selected from the group consisting of protoanemonin and furfural; and
 (iii) β-hydroxypropionic acid and/or acrylic acid dimer in an amount of 1 to 1000 ppm by weight relative to the weight of the acrylic acid;
the basic composition including a basic compound and iron,
the basic composition having an iron content of 0.14 to 3.5 ppm by weight, and
the water-absorbent resin having a liquid permeability under pressure (PPUP) in a range of 50 to 100%.

3. The process according to claim 1, after the step (a), further comprising:
 (b) a step of drying the hydrogel crosslinked polymer by application of heat; and
 (c) a step of subjecting the resultant hydrogel crosslinked polymer to surface cross-linking treatment by application of heat.

4. The process according to claim 1, wherein:
the basic compound is alkaline-metal hydroxide or alkaline-metal carbonate.

5. The process according to claim 1, wherein:
the basic compound is sodium hydroxide or sodium carbonate.

6. The process according to claim 1, wherein:
the acrylic acid included in the acrylic acid composition has an unpolymerizable organic compound content of 1 to 1000 ppm by weight, wherein the unpolymerizable organic compound has a solubility parameter of $(1.0 \times 10^4 \, (Jm^{-3})^{1/2}$ to $2.5 \times 10^4 \, (Jm^{-3})^{1/2}$.

7. The process according to claim 1, wherein:
a chelating agent is added to the acrylic acid composition or the hydrogel crosslinked polymer.

8. The process according to claim 1, wherein:
the iron is iron (III) oxide, and the amount of iron (III) oxide in the basic composition is 0.2 to 5.0 ppm by weight.

9. The process according to claim 1, wherein:
the acrylic acid included in the acrylic acid composition has: (I) a phenothiazine content of 0 to 0.1 ppm by weight relative to the weight of the acrylic acid; (II) at least one compound content of which is 0 to 5 ppm by weight relative to the weight of the acrylic acid, the compound being selected from the group consisting of aldehyde, except furfural, and maleic acid; and (III) at least one saturated carboxylic acid content of which is 10 to 800 ppm by weight relative to the weight of acrylic acid, the saturated carboxylic acid being selected from the group consisting of acetic acid and propionic acid.

10. The process according to claim 1, wherein:
the water-absorbent resin has an absorption capacity for a physiological saline solution under pressure (AAP 1.9 kPa) of not less than 20 g/g, and an absorption capacity for the physiological saline solution under pressure (AAP 4.9 kPa) of not less than 15 g/g.

11. The process according to claim 6, wherein:
the unpolymerizable organic compound is in advance added to or included in a cross-linking agent that is a component of the acrylic acid composition.

12. The process according to claim 2, after the step (a'), further comprising:
(b) a step of drying the hydrogel crosslinked polymer by application of heat; and
(c) a step of subjecting the resultant hydrogel crosslinked polymer to surface cross-linking treatment by application of heat.

13. The process according to claim 2, wherein:
the basic compound is alkaline-metal hydroxide or alkaline-metal carbonate.

14. The process according to claim 2, wherein:
the basic compound is sodium hydroxide or sodium carbonate.

15. The process according to claim 2, wherein:
the acrylic acid included in the acrylic acid composition has an unpolymerizable organic compound content of 1 to 1000 ppm by weight, wherein the unpolymerizable organic compound has a solubility parameter of $(1.0\times 10^4 \, (Jm^{-3})^{1/2}$ to $2.5\times 10^4 \, (Jm^{-3})^{1/2}$.

16. The process according to claim 2, wherein:
a chelating agent is added to the acrylic acid composition or the hydrogel crosslinked polymer.

17. The process according to claim 2, wherein:
the iron is iron (III) oxide, and the amount of iron (III) oxide in the basic composition is 0.2 to 5.0 ppm by weight.

18. The process according to claim 2, wherein:
the acrylic acid included in the acrylic acid composition has: (I) a phenothiazine content of 0 to 0.1 ppm by weight relative to the weight of the acrylic acid; (II) at least one compound content of which is 0 to 5 ppm by weight relative to the weight of the acrylic acid, the compound being selected from the group consisting of aldehyde, except furfural, and maleic acid; and (III) at least one saturated carboxylic acid content of which is 10 to 800 ppm by weight relative to the weight of acrylic acid, the saturated carboxylic acid being selected from the group consisting of acetic acid and propionic acid.

19. The process according to claim 2, wherein:
the water-absorbent resin is such that an absorption capacity for a physiological saline solution under pressure (AAP 1.9 kPa) is not less than 20 g/g; and an absorption capacity for a physiological saline solution under pressure (AAP 4.9 kPa) is not less than 15 g/g.

20. The process according to claim 15, wherein:
the unpolymerizable organic compound is in advance added to or included in a cross-linking agent that is a component of the acrylic acid composition.

21. The process according to claim 1, wherein the water-absorbent resin has a weight-average particle diameter of 200 to 600 μm before or after surface cross-linking and contains 3% by mass or less of particles having a particle diameter of 150 μm or smaller.

22. The process according to claim 2, wherein the water-absorbent resin has a weight-average particle diameter of 200 to 600 μm before or after surface cross-linking and contains 3% by mass or less of particles having a particle diameter of 150 μm or smaller.

* * * * *